United States Patent [19]
Howard, Jr.

[11] Patent Number: 5,821,245
[45] Date of Patent: Oct. 13, 1998

[54] USE OF NAPHTHALENE DERIVATIVES IN TREATING LUNG CARCINOMA

[75] Inventor: Harry R. Howard, Jr., Bristol, Conn.

[73] Assignee: Pfizer Inc., New York, N.Y.

[21] Appl. No.: 815,671

[22] Filed: Mar. 13, 1997

Related U.S. Application Data

[60] Provisional application No. 60/013,501 Mar. 15, 1996.

[51] Int. Cl.⁶ ........................ A61K 31/495; A61K 31/50
[52] U.S. Cl. ........................... 514/252; 514/255; 514/256
[58] Field of Search .................................... 514/256, 252, 514/255

[56] References Cited

FOREIGN PATENT DOCUMENTS 9406770 6/1994 WIPO.
9421619 9/1994 WIPO.

OTHER PUBLICATIONS

Cattaneo, Maria G., et al., "Mitogenic effect of serotonin in human cell lung carcinoma cells", European Journal of Pharmacology, Molecular Pharmacology Section 291, pp. 209–211 (1995).

Cattaneo, Maria G., et al., "5–HT$_{1D}$ receptor type is involved in stimulation of cell proliferation by serotonin in human small cell lung carcinoma", European Journal of Pharmacology, Molecular Pharmacology Section 268, pp. 425–430 (1994).

Ishibashi, Miyuki, et al., "Inhibition of Growth of Human Small Cell Lung Cancer by Bromocriptine", Cancer Research, 54, pp. 3442–3446, Jul. 1, 1994.

*Primary Examiner*—Jerome D. Goldberg
*Attorney, Agent, or Firm*—Peter C. Richardson; Paul H. Ginsburg; Mark Dryer

[57] ABSTRACT

A method of inhibiting cell growth in human small cell lung carcinoma comprising administering to a mammal in need of such treatment a cell growth inhibitory amount of a compound of the formula

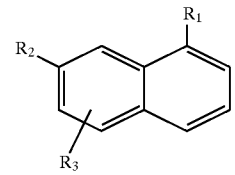

5 Claims, No Drawings

USE OF NAPHTHALENE DERIVATIVES IN TREATING LUNG CARCINOMA

This non-provisional application is based upon and claims priority from Provisional Application No. 60/013,501 filed Mar. 15, 1996.

BACKGROUND OF THE INVENTION

The present invention relates to the use of certain serotonin 5-$HT_{1D}$ receptor antagonists to inhibit cell growth in human small cell lung carcinoma.

WO 94 21619 (published Sep. 29, 1994) (hereinafter the "'619 publication") and U.S. patent application Ser. No. 08/308,320 (filed Sep. 19, 1994) (hereinafter the "'320 application") relate to certain naphthalene derivatives which are selective agonists and antagonists of serotonin 1 (5-$HT_1$) receptors. The '619 publication and the '320 application also relate to processes and intermediates for their preparation, to pharmaceutical compositions containing them and to their medicinal use in treating migraine and other disorders for which a 5-$HT_1$ agonist or antagonist is indicated.

M. Cattaneo et al. (European J. Pharmacology, Molecular Pharmacology Section 268, 425–430 (1994)) refers to the effect of serotonin agonists, especially 5-$HT_{1D}$ receptors agonists, on proliferation of small cell lung carcinoma (SCLC). The reference speculates that antagonists of 5-$HT_{1D}$ receptors might be useful in suppression of SCLC growth.

WO 94-06770 (published Mar. 31, 1994) relates to the use of certain N-cyano-$N^1$-pyridylguanidines, with serotonin 5-$HT_2$ receptor antagonist activity, as anti-neoplastic chemotherapeutic agents.

M. Ishibashi et al. (Cancer Research, 54, 3442–3446 (1994)) refers to the potential utility of the dopamine $D_2$ agonist, bromocriptine, as an inhibitor of growth of human SCLC.

SUMMARY OF THE INVENTION

The present invention relates to a method of inhibiting cell growth in human small cell lung carcinoma comprising administering to a mammal in need of such treatment a cell growth inhibitory amount of a compound of the formula

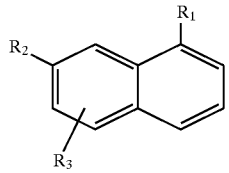

I where $R_1$ is of the formula

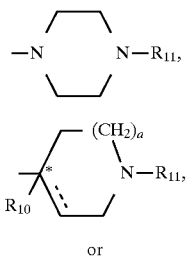

II

III or

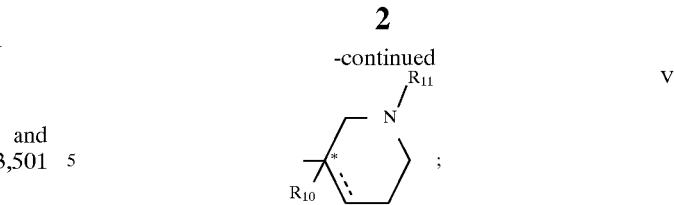

V $R_2$ is —$R_4$, —O—$R_4$, —O—S(O)$_2$—$R_4$, —$NR_4R_5$, $R_4$—(CH$_2$)$_b$—NH(C=X)—(CH$_2$)$_c$—, $R_4$—(CH$_2$)$_b$—O(C=O)NH—(CH$_2$)$_c$—(C=O)NH—, $R_4$—(C=O)NH—(C=O)NH—. —(CH$_2$)$_b$—NH(C=X)—(CH$_2$)$_c$—$R_4$, $R_4$—(CH$_2$)$_b$—O(C=O)—(CH$_2$)$_c$—, —(CH$_2$)$_b$—O(C=O)—(CH$_2$)$_c$—$R_4$, —NH(C=X)NH—$R_4$, $R_4$—O(C=O)O—, —O(C=O)NH—$R_4$, $R_4$—O(C=O)NH—, —(CH$_2$)$_b$—(C=O)—(CH$_2$)$_c$—$R_4$, —NH—S(O)$_2$—$R_4$, —C(OH)$R_4R_5$, —CH(OH)—$R_4$, —(C=O)—$NR_4R_5$, —CN, —NO$_2$, $R_4$—($CR_6R_7$)$_f$—O—($CR_8R_9$)$_g$—, substituted $C_1$ to $C_6$ alkyl, substituted or unsubstituted $C_1$ to $C_6$ alkenyl, or substituted or unsubstituted $C_1$ to $C_6$ alkynyl, said substituted moieties substituted with a moiety of the formulae —$R_4$, —$R_4R_5$, —O—$R_4$, or —S(O)$_d$—$R_4$;

$R_3$ is a substituent on any of the carbon atoms of the naphthalene ring capable of forming an additional bond and each occurrence of $R_3$ is independently selected from the group consisting of hydrogen, halogen, —CN, —NO$_2$, $C_1$ to $C_6$ alkyl, $C_1$ to $C_6$ alkoxy, $C_1$ to $C_6$ thioalkyl, —$R_{30}$, —$NR_{31}R_{32}$, —$CONR_{31}R_{32}$, —S(O)$_j$—$R_{30}$ and —$CO_2R_{30}$;

$R_4$ and $R_5$ are each independently

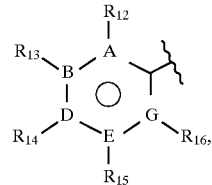

XV

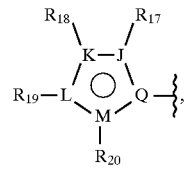

XVI

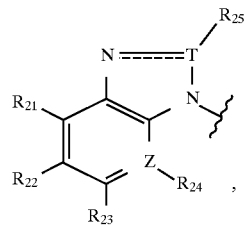

XVII hydrogen, —CF$_3$, $C_1$ to $C_6$ alkyl, or $C_1$ to $C_6$ alkylaryl, with the proviso that when $R_2$ is —$R_4$ or —$OR_4$, $R_4$ is not hydrogen or $C_1$ to $C_6$ alkyl;

$R_6$ and $R_7$ are independently selected from hydrogen, $C_1$ to $C_6$ alkyl, and when f is greater than 1 then each $R_6$ and $R_7$ is independently selected from any other $R_6$ or $R_7$;

$R_8$ and $R_9$ are independently selected from hydrogen, $C_1$ to $C_6$ alkyl optionally substituted with from one to seven fluorine atoms, preferably one to three fluorine atoms, and when g is greater than 1 then each $R_8$ and $R_9$ is independently selected from any other $R_8$ or $R_9$;

$R_{10}$ is hydrogen, $C_1$ to $C_6$ alkyl, —OH, or $C_1$ to $C_6$ alkoxy optionally substituted with from one to seven fluorine atoms (preferably one to three fluorine atoms); wherein said $C_1$ to $C_6$ alkyl group may also optionally contain one to three double or triple bonds;

$R_{11}$ is hydrogen, $C_1$ to $C_{10}$ alkyl, $-(CH_2)_m-aryl^1$, aryl, $-(CH_2)_m-(C_5$ to $C_7$ cycloalkyl), $-(CH_2)_n-R_{29}$, or $-CO_2R_{26}$, wherein said $aryl^1$ moiety may optionally be substituted with from one to three substituents independently selected from any of the substituents listed for $R_3$; and wherein said $C_5$ to $C_7$ cycloalkyl moiety may optionally be substituted with from one to three substituents independently selected from any of the substituents listed for $R_3$, with the proviso that when $R_{11}$ is $-CO_2R_{26}$, then $R_{26}$ is not hydrogen;

$R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are each independently H, halogen, $-CF_3$, $-(C=O)R_{26}$, $-CN$, $-OR_{26}$, $-NR_{26}R_{27}$, $-NR_{26}CO_2R_{28}$, $-N=C-N(CH_3)_2$, $-S(O)_eR_{26}$, $-SO_2NR_{26}R_{27}$, $-NO_2$, aryl, $C_1$ to $C_6$ alkylaryl, $-(C=O)OR_{26}$, $-(C=O)NR_{26}R_{27}$, $C_1$ to $C_6$ alkyl, $C_1$ to $C_5$ alkoxy, $C_1$ to $C_5$ alkylthio, formyl, $C_2$ to $C_6$ alkenyl, and $C_2$ to $C_6$ alkynyl, with the proviso that when $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, or $R_{24}$ are $-(C=O)OR_{26}$ or $-S(O)_eR_{26}$, then $R_{26}$ is not hydrogen;

$R_{12}$ and $R_{13}$, $R_{13}$ and $R_{14}$, $R_{14}$ and $R_{15}$, $R_{15}$ and $R_{16}$, $R_{17}$ and $R_{18}$, $R_{18}$ and $R_{19}$, $R_{19}$ and $R_{20}$, $R_{21}$ and $R_{22}$, $R_{22}$ and $R_{23}$, and $R_{23}$ and $R_{24}$ may be taken together to form a five-to-seven-membered alkyl ring, a six-membered aryl ring, a five to seven membered heteroalkyl ring having one heteroatom of N, O, or S, or a five- to six-membered heteroaryl ring have 1 or 2 heteroatoms of N, O, or S;

$R_{25}$ is hydrogen or $C_1$ to $C_3$ alkyl;

$R_{26}$, and $R_{27}$ are each independently hydrogen, $C_1$ to $C_6$ alkyl, aryl, or $C_1$ to $C_6$ alkylaryl, or $R_{26}$ and $R_{27}$ may be each taken together to form a $C_4$ to $C_7$ alkyl ring;

$R_{28}$ is $C_1$ to $C_6$ alkyl, aryl, or $C_1$ to $C_6$ alkylaryl;

$R_{29}$ is $-OR_{26}$, $-C(=O)NR_{26}R_{27}$, $-(C=O)OR_{26}$, $-CN$, $-NR_{26}C(=O)R_{27}$, or $-O(C=O)R_{26}$, with the proviso that when $R_{29}$ is $-(C=O)OR_{26}$ or $-O(C=O)R_{26}$, then $R_{26}$ is not hydrogen;

$R_{30}$ is hydrogen, $C_1$ to $C_6$ alkyl, aryl, $C_1$ to $C_6$ alkylaryl, $-(C=O)-aryl$;

$R_{31}$ and $R_{32}$ are each independently hydrogen, $C_1$ to $C_6$ alkyl, or $C_1$ to $C_6$ alkylaryl, or $R_{31}$ and $R_{32}$ may be taken together to form a three- to eight-membered heteroaryl ring having 0, 1, 2, or 3 heteroatoms of N, O, or S;

A, B, D, E, and G are each independently C, N, or (C=O);

J, K, L and M are each independently C, N, O, S, or (C=O), with the proviso that there is at most one of O, (C=O), or S per ring;

Q and Z are each independently C or N;

T is C, N, or (C=O);

X is O or S;

a is 1 or 2;

e is 0, 1 or 2;

d is 0, 1, or 2;

b and c are each independently 0, 1, 2, 3, 4, 5, or 6, with b+c being at most 6, with the proviso that when $R_2$ is $R_4-(CH_2)_b-O(C=O)NH-(CH_2)_c-(C=O)NH-$ and $R_4$ is hydrogen, then b is not 0;

f and m are each independently 0, 1, 2, 3, 4, 5 or 6;

g and n are each independently 0, 1, 2 or 3;

j is 0, 1 or 2;

a broken line indicates the presence optionally of a double bond, a chiral carbon is designated by *, and the above aryl groups and the aryl moieties of the above alkylaryl groups are independently selected from phenyl, substituted phenyl, naphthyl, and substituted naphthyl wherein said substituted phenyl and substituted naphthyl may each be substituted with one to three groups selected from $C_1$ to $C_4$ alkyl, halogen, hydroxy, cyano, carboxamido, nitro, and $C_1$ to $C_4$ alkoxy, or a pharmaceutically acceptable salt thereof. The compounds of formula I, as defined above, are hereinafter also referred to as the "active compounds."

Compounds of formula I where $R_4$ or $R_5$ includes a nitrogen atom which is connected to an $R_2$ moiety including an oxygen atom such that the nitrogen atom and the oxygen atom are directly connected or connected by a methylene group may not be sufficiently stable to be used as drug compounds. Any such unstable compounds do not form part of the invention.

The active compounds of the present invention include all stereoisomers and all optical isomers of the formula I (e.g., R and S enantiomers) and their racemic and diastereomeric mixtures. When $R^1$ is a group of the formula III or V

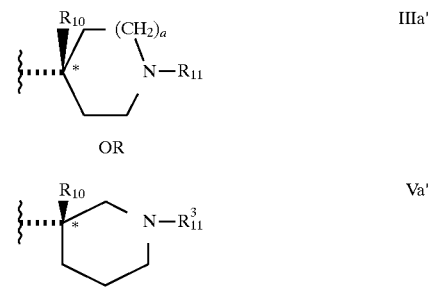

the R enantiomers (e.g., IIIa' and Va') at the chiral carbon designated by an asterisk in the ring in which "R" occurs are preferred.

Unless otherwise indicated, the alkyl and alkenyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties. Unless otherwise indicated, halogen includes fluorine, chlorine, bromine, and iodine.

The following compounds are preferred:

7-Benzamido-1-(4-methyl-1-piperazinyl)-naphthalene;
7-(1-Naphthylcarboxamido)-1-(4-methyl-1-piperazinyl)-naphthalene;
7-Benzamido-1-(1-piperazinyl)-naphthalene;
7-Acetamido-1-(4-methyl-1-piperazinyl)-naphthalene;
7-Hexanamido-1-(4-methyl-1-piperazinyl)-naphthalene;
7-(Phenylaminocarbonylamino)-1-(4-methyl-1-piperazinyl)-naphthalene;
7-(Benzyloxycarbonylamino)-1-(4-methyl-1-piperazinyl)-napthalene;
7-(3-Nitro-2-pyridinylamino)-1-(4-methyl-1-piperazinyl)-naphthalene;
7-(5-Nitro-2-pyridylamino)-1-(4-methyl-1-piperazinyl)-naphthalene;
7-(3-Hydroxy-3-methyl-1-butynyl)-1-(4-methyl-1-piperazinyl)-naphthalene;
7-(2-Ethylsulfonyl)ethenyl-1-(4-methyl-1-piperazinyl)-napthalene;
7-(3-Methylaminosulfonylphenyl)-1-(4-methyl-1-piperazinyl)naphthalene;
7-Benzoyl-1-(4-methyl-1-piperazinyl)naphthalene;
7-(3-Methoxycarbonylphenyl)-1-(4-methyl-1-piperazinyl)-napthalene;
7-(3-Fluorophenyl)-1-(4-methyl-1-piperazinyl)-napthalene;
7-(Benzyloxy)-1-(4-methyl-1-piperazinyl)-naphthalene;

7-(4-Chlorobenzoyloxy)-1-(4-methyl-1-piperazinyl)-napthalene;
7-(Imidazolo[4,5-b]pyridin-1-yl)-1-(4-methyl-1-piperazinyl)-naphthalene;
7-(Benzimidazol-1-yl)-1-(4-methyl-1-piperazinyl)-naphthalene;
7-(5-Cyanobenzimidazol-1-yl)-1-(4-methyl-1-piperazinyl)-naphthalene;
7-(5-Trifluoromethylbenzimidazol-1-yl)-1-(4-methyl-1-piperazinyl)-naphthalene;
7-(6,7-Dichlorobenzimidazol-1-yl)-1-(4-methyl-1-piperazinyl)-naphthalene;
2-[8-(4-Methylpiperazin-1-yl)naphthalen-2-yloxymethyl]quinoline;
1-Methyl-4-{7-[2-(4-chlorophenyl)thiazol-5-ylmethoxy]naphthalen-1-yl}piperazine;
1-Methyl-4-[7-(5-chloro-thiophen-2-ylmethoxy)naphthalen-1-yl]piperazine;
8-(4-Methylpiperazin-1-yl)naphthalene-2-carboxylic acid phenylamide;
7-Amino-1-(1-methyl-4-piperidinyl)-naphthalene;
7-(3-Nitro-2-pyridylamino)-1-(1-methyl-4-piperidinyl)-naphthalene;
7-(Imidazolo[4,5-b]pyridin-1-yl)-1-(1-methyl-4-piperidinyl)-naphthalene;
7-(4-Chlorobenzamido-1-(1-methyl-4-piperidinyl)-naphthalene;
7-Amino-1-(1-methyl-3-piperidinyl)-naphthalene;
7-(3-Nitro-2-pyridylamino)-1-(1-methyl-3-piperidinyl)-naphthalene;
7-(Imidazolo[4,5-b]pyridin-1-yl)-1-(1-methyl-3-piperidinyl)-naphthalene;
7-Benzamido-1-(1-methyl-3-piperidinyl)-naphthalene;
7-(4-Chlorobenzamido)-1-(4-methoxyethyl-1-piperazinyl)-naphthalene;
7-(4-Chlorobenzamido)-1-($^4$-propyl-1-piperazinyl)-naphthalene;
7-(4-Chlorobenzamido)-1-(4-ethyl-1-piperazinyl)-naphthalene;
7-Amino-1-(1-piperazinyl)-naphthalene;
7-(Imidazolo-[4,5-b]-pyridin-1-yl)-1-(1-piperazinyl)-naphthalene; and
7-(1,2,3-Triazolo-[4,5-b]-pyridin-1-yl)-1-(1-piperazinyl)-naphthalene;
1-{7-[5-(2-methoxyphenyl)-[1,2,4]oxadiazol-3-ylmethoxy]-naphthalen-1-yl}-4-methylpiperazine;
1-[7-(5-tert-butyl-[1,2,4]oxadiazol-3-ylmethoxy)-naphthalen-1-yl]-4-methylpiperazine;
1-methyl-4-[7-(3-phenyl-[1,2,4]oxadiazol-5-ylmethoxy)-naphthalen-1-yl]-piperazine;
1-methyl-4-[7-(5-phenyl-[1,2,4]oxadiazol-3-ylmethoxy)-naphthalen-1-yl]-piperazine;
1-{7-[5-(3-methoxyphenyl)-[1,2,4]oxadiazol-3-ylmethoxy]-naphthalen-1-yl}-4-methylpiperazine;
1-{7-[5-(3,5-dimethylisoxazol-4-yl)-[1,2,4]oxadiazol-3-ylmethoxy]-naphthalen-1-yl}-4-methylpiperazine;
1-{7-[3-(4-methoxyphenyl)-[1,2,4]oxadiazol-5-ylmethoxy]-naphthalen-1-yl}-4-methylpiperazine;
2-[8-(1-methylpiperidin-4-yl)-naphthalen-2-yloxy]-pyrimidine;
1-methyl-4-[7-(3-pyridin-3-ylmethyl-[1,2,4]oxadiazol-5-yl)-naphthalen-1-yl]-piperazine; and
1-methyl-4-[7-(pyridin-2-ylmethoxy)-naphthalen-1-yl]-piperazine.

The following compounds are particularly preferred:
7-(Imidazolo[4,5-b]pyridin-1-yl)-1-(1-methylpyrrolidin-3-yl)naphthalene;
2-[8-(4-Methylpiperazin-1-yl)naphthalen-2-yloxy]nicotinonitrile;
1-(4-Methylpiperazin-1-yl)-7-pyrimidin-5-yl)naphthalene;
7-(4-Chlorobenzamido-1-(4-methylpiperazin-1-yl)naphthalene;
7-(3-Methoxyphenyl)1-(4-methylpiperazin-1-yl)naphthalene;
8-(4-Methylpiperazin-1-yl)naphthalene-2-carboxylic acid 4-chlorobenzylamide;
7-Pyrimidin-2-yloxy-1-(4-methylpiperazin-1-yl)naphthalene;
7-(4-Methoxyphenyl)-1-(4-methylpiperazin-1-yl)-naphthalene; and
8-(1-Methylpiperidin-4-yl)naphthalene-2-carboxylic acid 4-chlorobenzylamide.

Other compounds believed to be more preferred are the following:
1-{7-[3-(4-Chloro-benzyl)-[1,2,4]oxadiazol-5-yl]-naphthalen-1-yl}-4-methyl-piperazine;
4-{7-[3-(4-Chloro-benzyl)-[1,2,4]oxadiazol-5-yl]-naphthalen-1-yl}-1-methyl-piperidine;
7-(3-Methoxyphenyl)-1-(1-methylpiperidin-4-yl)-naphthalene; and
7-(4-Methoxyphenyl)-1-(1-methylpiperidin-4-yl)-naphthalene.

DETAILED DESCRIPTION OF THE INVENTION

The compounds of formula I are produced using processes disclosed in the '619 publication and '320 application, and the disclosure of both of these is hereby incorporated by reference.

Compounds of formula I of the '320 application may be prepared according to the following schemes and related discussion.

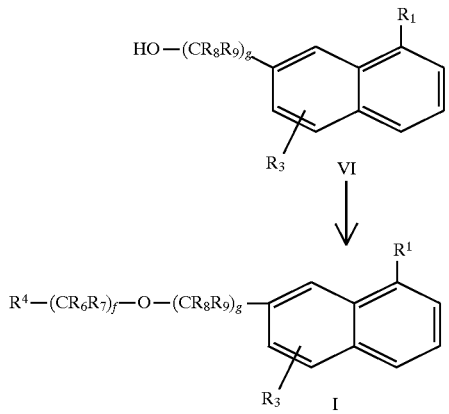

SCHEME 1

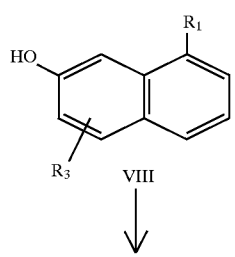

SCHEME 2

5,821,245
7
-continued
SCHEME 2
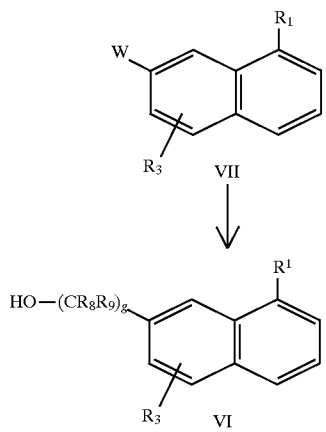
SCHEME 3
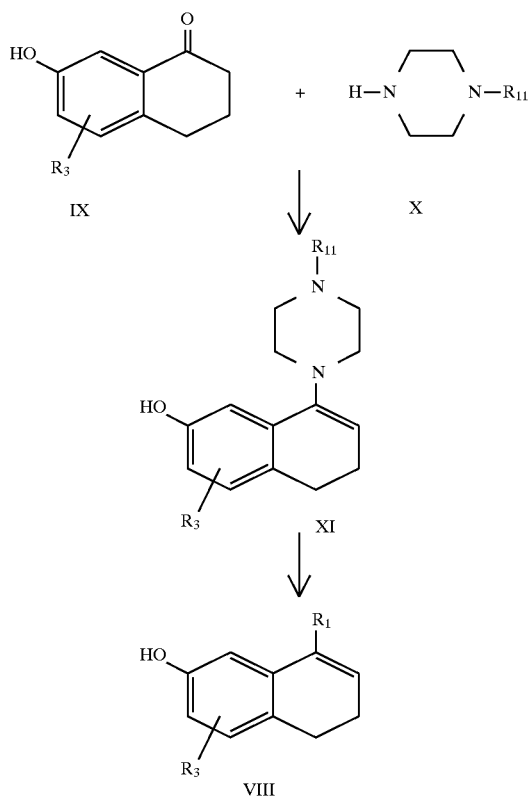
SCHEME 4
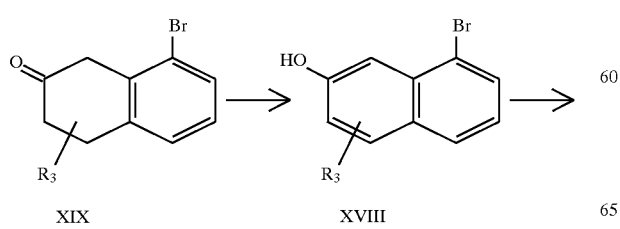
8
-continued
SCHEME 4
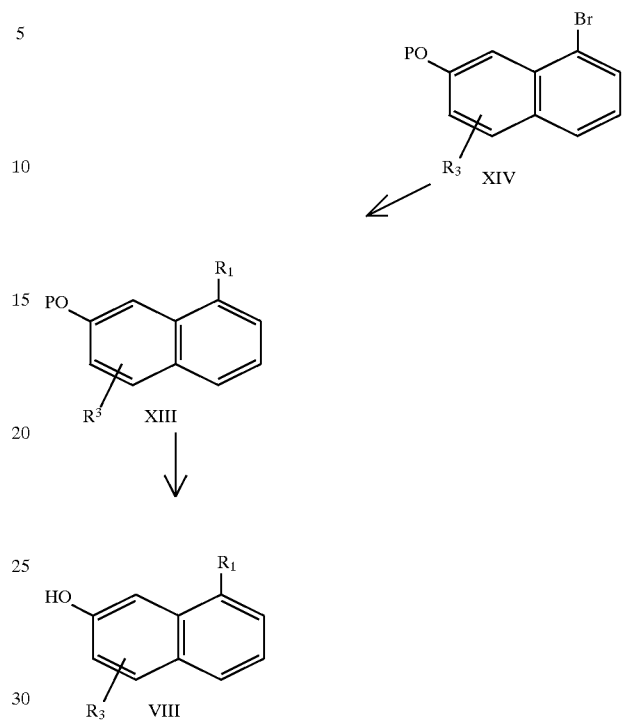
SCHEME 5
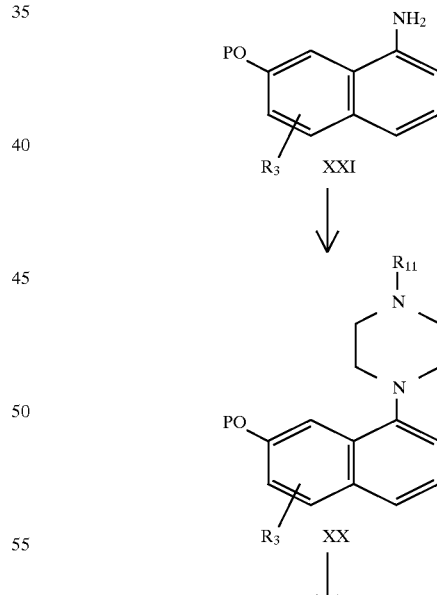
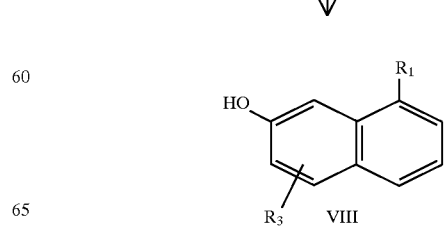

According to Scheme 1, compounds of the general formula I may be prepared by alkylation of an intermediate of formula VI with a compound of the general formula $$R^4—(CR_6R^7)_5—Y$$

wherein Y is a suitable leaving group such as chloro, bromo, iodo, $—OSO_2Ph$, $—OSO_2PhCH_3$, $—OSO_2CH_3$, $—OSO_2CF_3$ (trifluoromethanesulfonyloxy) or OH.

The alkylation reaction may be carried out in the presence of a base such as triethylamine, sodium or potassium carbonate or bicarbonate, sodium or potassium hydride or 4-dimethylaminopyridine. A suitable solvent for the reaction can be selected from non-protic solvents such as diethyl ether, tetrahydrofuran (THF), 1,4-dioxane, chloroform ($CHCl_3$), dichloromethane ($CH_2Cl_2$), N,N-dimethylformamide (DMF), N,N-dimethylacetamide, N-methypyrrolidinone, benzene, toluene or xylenes. The reaction can be performed at a temperature of about 0° C. to about the boiling point of the solvent employed (e.g. about 100° C. for DMF) and at a pressure of about one to about three atmospheres.

Preferably, the reaction is conducted in N,N-dimethylformamide with sodium hydride as a base at a temperature of about 25°–100° C. and one atmosphere of pressure.

Alternatively, compounds of the formula I can be prepared from compounds of formula VI by Mitsunobu chemistry. According to this method, compounds of formula VI are reacted with alcohols, for example, 2-pyrazinemethanol or 4-pyrazolemethanol in the presence of triphenylphosphine and a dialkyl azodicarboxylate, preferably diethyl azodicarboxylate. Mitsunobu reactions are known in the art, for example, as disclosed in *Synthesis,* 1981, 1.

According to the methods of Scheme 2, compounds of the formula VI can be prepared from compounds of the formula VIII. Compounds of the formula VI can then be transformed into compounds of the formula I according to the procedures of Scheme 1.

Compounds of the formula VIII are converted into a triflate ($CF_3SO_3$) of the formula VII wherein W is $CF_3SO_3—$ by reaction with an activated form of triflic acid, for example, triflic anhydride, acid chloride or N-phenyltrifluoromethanesulfonimide, preferably triflic anhydride. Typically, this reaction is performed in the presence of a base, such as, for example, triethylamine or diisopropylethylamine, preferably triethylamine. The reaction may be run in an inert solvent, such as tetrahydrofuran or methylene chloride, at a temperature of from about −78° C. to about 25° C., preferably below about 0° C. This procedure is known in the art, as shown, for example, in *J. Amer. Chem. Soc.,* 1987, 109, 5478.

The compound of formula VII can then be transformed into a compound of formula VII wherein W is an ester of the formula $—CO_2R$, wherein R is ($C_1–C_6$) alkyl or benzyl, by reaction with carbon monoxide in the presence of a palladium catalyst in an alcohol solvent such as methanol. The catalyst may be selected from those typically employed for the so-called Heck reaction (palladium acetate, palladium chloride, bis(acetonitrile)palladium chloride, for example). The reaction is carried out neat or in an alcohol solvent such as methanol, ethanol, isopropanol, butanol or benzyl alcohol. The reaction is conveniently run at 20° C. to 100° C., preferably 60° C. to 100° C. The details of reactions of this type have been well described in the literature *(Organic Reactions* 1982, 27, 345).

The ester of formula VII wherein W is $—CO_2R$ can then be reduced with a catalyst to form a hydroxymethyl compound of formula VI wherein g is one and $R_8$ and $R_9$ are hydrogen. The reduction of an ester group to a hydroxymethyl group is well known to those of ordinary skill in the art. Preferably, the ester is reduced using borane-tetrahydrofuran complex in an inert solvent such as tetrahydrofuran (THF).

This alcohol of formula VI wherein g is one can be converted into other alcohols of formula VI by processes well known to those of ordinary skill in the art. Specifically, the alcohol of formula VI wherein g is one can be converted into a compound of formula VI wherein g is two by reacting the alcohol with an activating group such as methanesulfonyl chloride in triethylamine (TEA) in an inert solvent such as methylene chloride ($CH_2Cl_2$) to generate an activated leaving group in which the alcohol has been replaced by $CH_3SO_3—$, and then treating the activated leaving group with a nucleophile such as sodium or potassium cyanide in a solvent such as dimethyl sulfoxide to form a cyano intermediate of the formula

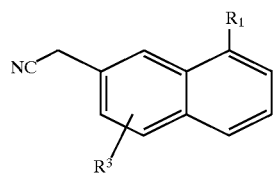

The cyano group can then be hydrolyzed under acidic conditions to produce a carboxylic acid. The acid can in turn be converted into an ester by methods familiar to those of ordinary skill in the art. For example, the acid can be reacted with an alcohol of the formula ROH, wherein R is as defined above, in the presence of an acid catalyst to produce an ester. The ester can be reduced to the compound of formula VI wherein g is two in a manner similar to the reduction of the ester to the compound of formula VI wherein g is one.

According to the methods of Scheme 3, compounds of formula VIII wherein $R^1$ is piperazine are prepared by reaction of an α-tetralone of formula IX with a suitable piperazine of formula X to form an enamine of formula XI, which is then oxidized to the compound of formula VIII.

The enamines of formula XI are generally prepared by reaction of a compound of formula IX with a compound of formula X in the presence of an acid catalyst such as, for example, p-toluenesulfonic acid or titanium tetrachloride. If desired, the water formed as a by-product of the reaction may be effectively removed from the reaction as it is formed by the use of a drying reagent such as molecular sieves or calcium sulfate, or by azeotropic removal employing a Dean Stark trap with a refluxing solvent. The reaction is typically run in a reaction inert solvent such as benzene, toluene, tetrahydrofuran, or methylene chloride, at a temperature of from about −78° C. to about 150° C. When titanium tetrachloride is used as the acid catalyst, the preferred temperature for the reaction is from about −78° C. to about 25° C. When azeotropic water separation is employed, the preferred reaction temperature is the boiling temperature of the particular reaction solvent.

In general, the α-tetralones of formula IX are known in the literature or can be readily prepared by those skilled in the art. A typical preparation is that described for 7-hydroxy-α-tetralone, *(Tetrahedron Lett.,* 1981, 22, 603). Other α-tetralones of formula IX are readily prepared using the alkylation, acylation, and organometallic reactions described herein and in standard synthesis texts, for example *Organic Synthesis,* Wiley, N.Y. The piperazines of formula X are commercially available or can be made using methods known in the art.

The enamines of formula XI may be converted to compounds of formula VIII by an oxidative process. The reaction may be carried out using a variety of methods known in the art. Among the acceptable oxidizing agents are noble metal catalysts such as palladium or platinum on activated carbon if desired, chloranil, and sulfur. Preferably, the oxidizing agent is palladium on activated carbon. The reactions can be carried out in a reaction inert solvent for example, toluene, xylene, tetrahydrofuran, methylene chloride, preferably toluene or xylene, however a solvent is not always necessary, especially for oxidations carried out with elemental sulfur. The preferred solvent is toluene. The oxidation reactions generally proceed at a temperature of about 0° C. to about 250° C. Preferred temperatures for the oxidation depend on the particular oxidant in use and are about 60° C. to about 150° C. for noble metal catalytic oxidation, about 150° C. to about 250° C. for sulfur oxidation and about 0° C. to about 100° C. for chloranil oxidations.

The compounds of formula VIII wherein $R^1$ is a group of the formula III or V (i.e., tetrahydropyridine, piperidine, or azacycloalkylmethyl) can be made from 8-bromo-β-tetralone according to the procedures in U.S. Pat. No. 4,897,405, or by the methods described in Scheme 4.

According to Scheme 4, an 8-bromo-β-tetralone of the formula XIX is first oxidized (dehydrogenated) to form a 7-hydroxy-1-bromo-naphthalene of the formula XVIII using an oxidizing reagent, such as, for example, elemental sulfur as described above for the oxidation of the enamine of formula XI in Scheme 3. An appropriate protecting group is then used to protect the hydroxyl group to form a compound of the formula XIV. Formation and selection of the appropriate protecting group are within the knowledge of one skilled in the art (e.g., Greene and Wuts, *Protective Groups in Organic Synthesis*, 2nd Edition, Wiley, N.Y. 1991). Preferably, the hydroxy protecting group is the t-butyl dimethylsilyl group.

After the hydroxy group has been protected, the bromo naphthalenes of the formula XIV are treated with a vinyl-stannane of the formula

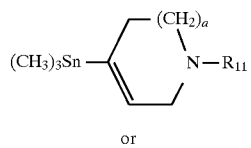

or

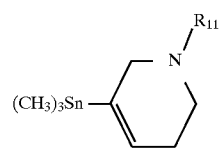

in the presence of a catalyst, preferably tetrakis (triphenylphosphine)palladium (($Ph_3P)_4Pd$) or tris (dibenzylidene acetone)dipalladium ($Pd_2(dba)_3$), a ligandless catalyst (*Tet. Letters*, 34, 4243 (1991)), either alone or with an added phosphine or arsine ligand (*JACS*, 113, 9585 (1991)) in a Stille reaction to form a compound of the formula XIII wherein $R^1$ is IIIb or Vb

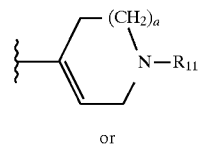

or

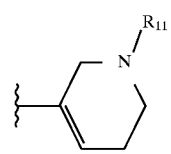

The procedures and conditions to carry out these reactions are known to those skilled in the art, including, for example, in *Angew. Chem. Int. Ed. Engl.*, 25, 508 (1986). A variation in which a triflate is used is also known to one skilled in the art, including, for example, in *J. Amer. Chem. Soc.*, 109, 5478 (1987). Another variation of this type of process using an alkyl or aryl halide in the presence of carbon monoxide gas and a palladium catalyst is also known, including, for example, in *J. Amer. Chem. Soc.*, 110, 1557 (1988).

The hydroxy protecting group in formula XIII can then be removed to form a compound of the formula VIII. Selection of the appropriate reagents and conditions to remove the suitable protecting groups is within the knowledge of one skilled in the art (e.g., Greene and Wuts, *Protective Groups in Organic Synthesis*, 2nd Edition, Wiley, N.Y. 1991).

Compounds of formula I wherein $R^1$ is a saturated heterocycle (i.e., piperidine) can be prepared by catalytic hydrogenation of a compound of formula XIII, using standard methods known to one skilled in the art, generally with palladium on carbon as the catalyst.

Compounds of formula I having an enantiomerically pure group at the $R^1$ position (i.e., of the formula IIIa' or Va' as described above) can be prepared using stereoselective reduction of a compound of the formula XIII. The stereoselective reduction is effected by treatment of the compound of the formula XIII with a binaphthyl-ruthenium catalyst, such as, for example, [(R)-2,2'-bis(diphenylphosphino)-1, 1'-binaphthyl]ruthenium diacetate according to the method of Takaya et. al. in *Organic Synthesis*, 72 D. L. Coffen editor, 74–85, (1993).

As an alternative, the 1-bromo-7-hydroxy-protected-naphthalene compounds of formula XIV from Scheme 4 may be treated with alkyllithium reagents, such as, for example, butyllithium, sec-butyllithium or tert-butyllithium, preferably butyllithium in an inert solvent, as shown below,

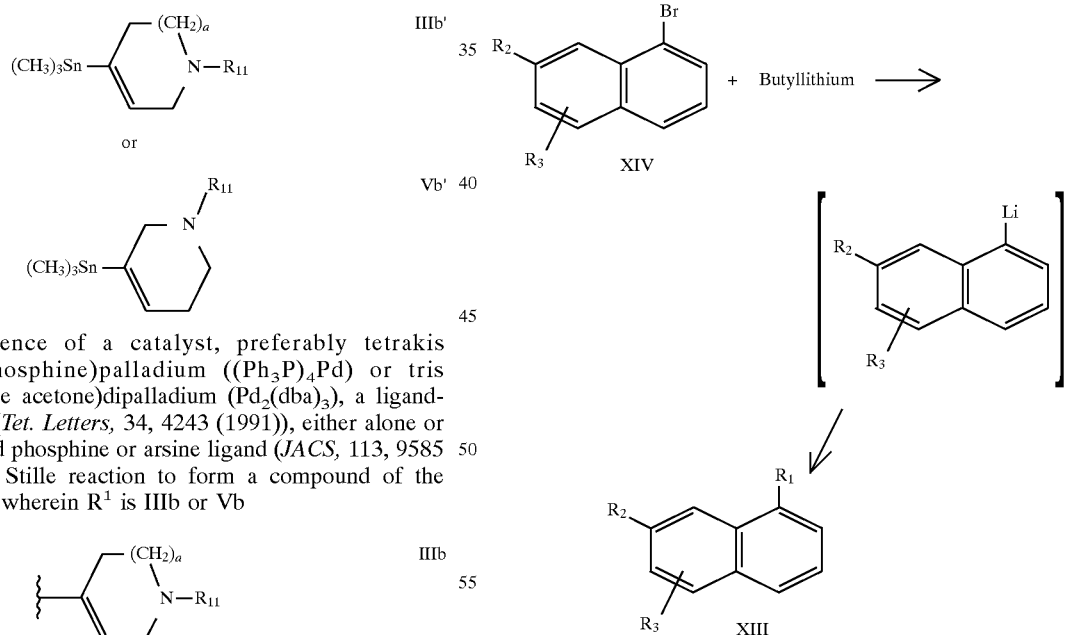

Suitable solvents include ether or tetrahydrofuran, preferably tetrahydrofuran. The reaction is generally run at a temperature of from about −110° C. to about 0° C. The intermediate lithium anions thus formed may then be further reacted with a suitable electrophile, selection of which depends on the substituents at the $R_1$ and $R_2$ positions. Suitable electrophiles to prepare hydroxy protected compounds of formula XIII include, for example, carbonyl derivatives or alkylating agents such as 1-BOC-4-piperidone or 1-BOC-prolinal. BOC is understood by those of ordinary skill in the art to refer to butoxycarbonyl.

After the bromo substituent has been functionalized, the hydroxyl protecting group may be removed using procedures well know in the art to form compounds of the formula VIII wherein $R^1$ is tetrahydropyridine or piperidine. The free hydroxyl group can then be derivatized to form compounds of the formula VI as described in Scheme 2.

Compounds of the formula VIII can also be prepared according to the methods of Scheme 5 through condensation of a protected or unprotected hydroxy compound of the formula XXI with a compound of the formula

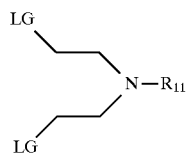

LG is a suitable $S_N2$ leaving group, such as, for example, chloro, bromo, iodo, $-OSO_2Ph$, $-OSO_2PhCH_3$, $-OSO_2CH_3$, $-OSO_2CF_3$ to form a hydroxy protected compound of the formula XX, preferably iodo. The reaction is performed in an inert solvent in the presence of base. The iodo leaving group is prepared in situ from the chloro derivative using stoichiometric amounts of sodium or potassium iodide in the reaction mixture. Suitable solvents include ($C_1$ to $C_4$) alcohols, dimethyl sulfoxide, N,N-dimethylformamide, N-methylpyrrolidinone, acetonitrile, and acetone. Acetonitrile is preferred. Suitable bases include sodium hydroxide, potassium hydroxide, triethylamine, sodium or potassium carbonate, cesium carbonate, and sodium or potassium hydrogen carbonate, preferably, sodium hydrogen carbonate. The reaction is usually conducted at a temperature of from about 50° C. to about 154° C., preferably from about 70° C. to about 90° C.

The hydroxy protected compound of the formula XX can be deprotected according to methods well known to those of ordinary skill in the art, to form a compound of the formula VIII (e.g., Greene and Wuts, *Protective Groups in Organic Synthesis,* 2nd Edition, Wiley, N.Y. 1991). Compounds of the formula VIII can be converted into compounds of the formula I according to the methods of Schemes 1 and 2.

Compounds of the formula I wherein $R_3$ is other than hydrogen can be prepared from other compounds of formula I wherein $R_3$ is bromine by methods well known to those of ordinary skill in the art. Compounds of formula I wherein $R_3$ is bromine can be made by processes analogous to those described in Preparation 1.

Unless indicated otherwise, the pressure of each of the above reactions is not critical. Generally, the reactions will be conducted at a pressure of about one to about three atmospheres, preferably at ambient pressure (about one atmosphere).

The compositions useful in the method of the present invention may be formulated in a conventional manner using one or more pharmaceutically acceptable carriers. Thus, the active compounds useful in the method of the present invention may be formulated for oral, buccal, intranasal, parenteral (e.g., intravenous, intramuscular or subcutaneous) or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate) ; or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia) ; non-aqueous vehicles (e.g. almond oil, oily esters or ethyl alcohol); and preservatives (e.g. methyl or propyl p-hydroxybenzoates or sorbid acid).

For buccal administration the composition may take the form of tablets or lozenges formulated in conventional manner.

The active compounds may be formulated for parenteral administration by injection, including using conventional catheterization techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

For intranasal administration or administration by inhalation, the active compounds are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds for oral, parenteral or buccal administration to the average adult human for use in practicing the claimed invention is 0.1 to 400 mg of the active ingredient per unit dose which could be administered, for example, 1 to 4 times per day.

The ability to inhibit the growth of SCLC can be evaluated using assays based upon those disclosed in M. Ishibashi, et al., *Cancer Research,* 54, 3442–3446 (1994). The assay involves growing a SCLC cell line, such as NCI-H69, a known human SCLC cell line which can be obtained from the American Type Culture Collection (Rockville, Md.). NCI-H69 can be grown in RPMI 1640 media supplemented with 10% fetal calf serum in a humidfied atmosphere of 5% $CO_2$ and 95% air at 37° C., which are collected, resuspended, and injected into athymic nude mice. After tumors have grown, they are removed, and used as donor tumors.

The donor tumors are then cut into pieces of approximately 2.0 mm in size and one piece is placed into the left rear flank of female athymic nude mice at the age of seven weeks and having a weight of from between 20 to 22g. Ten mice are divided into a control group (given normal food), as well as a low dose group and a high dose group, where the test compound is administered, for example, in food. The sizes of the tumor which are grown are measured periodically and when the largest tumor reaches a given size (e.g. 600mm$^2$), the entire group of mice are sacrificed and the tumors removed. The tumors are evaluated by weight, as well as by examination using electron microscopy to look for degenerative changes in the tumor, including, for example, pyknosis.

EXAMPLE 1

1-Methyl-4-[7-(5-phenyl-[1,2,4]oxadiazol-3-ylmethoxy)-naphthalen-1-yl]-piperazine dihydrochloride dihydrate To a solution of 80 mg (3.33 mmol) of oil free sodium hydride in 2.0 mL of anhydrous N,N-dimethylformamide (DMF) was added 400 mg (1.65 mmol) of 1-(7-hydroxynaphthyl)-4-methylpiperazine in 4.0 mL of DMF. After stirring at room temperature for 20 min, a solution of 380 mg (1.95 mmol) of the reactant 5-chloromethyl-3-phenyl-1,2,4-oxadiazole in 2.0 mL of DMF was added and the mixture was heated at 90° C. for 16 hr. The reaction was then cooled to room temperature and poured into approximately 50 ml of H$_2$O. After stirring for 20 min, the product was extracted into diethyl ether, which was washed with H$_2$O, dried over MgSO$_4$ and evaporated to a red oil. Chromatography on silica gel, using methanol/concentrated ammonium hydroxide/methylene chloride (CH$_3$OH: conc. NH$_4$OH: CH$_2$Cl$_2$) (2.5:0.5:97) gave the pure free base as a light yellow oil. The oil was dissolved in ethyl acetate and treated with hydrogen chloride gas (HCl) saturated ethyl acetate which, after standing for approximately 30 min, precipitated the title product as a colorless solid, 311 mg (47%), M.p. 82° C.

$^1$H-NMR (CDCl$_3$, free base) δ2.5 (s, 3H), 2.7 (bs, 4H), 3.1 (bs, 4H), 5.2 (s, 2H), 6.5 (d, 1H), 7.1 (dd, 1H), 7.2–7.6 (m, 9H), 7.7 (d, 1H).

Mass Spectrum (m/e, %): 401 (m$^{-1}$, 100), 373(5), 272, 255, 243.

Analysis calculated for C$_{24}$H$_{24}$N$_4$O$_2$•2HCl•2H$_2$O: C, 56.58; H, 5.94; N, 11.00. Found: C, 56.36; H, 6.21; N, 10.87.

By a method similar to Example 1 except that the reactant is different, the following compounds of Examples 2–40 were similarly prepared:

EXAMPLE 2

1-Methyl-4-[7-(1-phenyl-1H-tetrazol-5-yloxy)-naphthalen-1-yl]-piperazine dihydrochloride Mp 219° C. (dec).

$^1$H NMR (CDCl$_3$) δ 2.4 (s, 3H), 2.7 (bs, 4H), 3.2 (bs, 4H), 7.2 (d, 1H), 7.4 (m, 2H), 7.6 (m, 4H), 7.9 (m, 3H), 8.3 (d, 1H).

Mass spectrum: m/e 387 (M$^{+1}$)

Analysis calculated for C$_{22}$H$_{22}$N$_6$O•2HCl: C, 57.52; H, 5.27; N, 18.29. Found: C, 57.78; H, 5.27; N, 18.40.

EXAMPLE 3

1-Methyl-4-{7-[5-(3-trifluoromethylphenyl)-[1,2,4]oxadiazol-3-ylmethoxy]-naphthalen-1-yl}-piperazine dihydrochloride MP 175° C. (dec).

$^1$H NMR (CDCl$_3$) δ 2.4 (s, 3H), 2.8 (bs, 4H), 3.2 (bs, 4H), 5.5 (s, 2H), 7.1 (d, 1H), 7.3 (m, 2H), 7.5 (d, 1H), 7.7 (t, 2H), 7.8 (d, 1H), 7.9 (d, 1H), 8.3 (d, 1H), 8.5 (d, 1H).

Mass spectrum: m/e 387 (M$^{+1}$).

Analysis calculated for C$_{25}$H$_{23}$F$_3$N$_4$O$_2$•2HCl•H$_2$O: C, 53.67; H, 4.87; N, 10.02. Found: C, 53.64; H, 5.27; N, 9.86.

EXAMPLE 4

1-{7-[5-(3-Methoxyphenyl)-[1,2,4]oxadiazol-3-ylmethoxyl-naphthalen-1-yl}-4-methylpiperazine dihydrochloride hydrate Mp 174° C. (dec).

$^1$H NMR (CDCl$_3$) δ 2.5 (s, 3H), 2.7 (bs, 4H), 3.2 (bs, 4H), 4.0 (s, 3H), 5.5 (s, 2H), 7.1 (m, 2H), 7.3 (m, 2H), 7.5 (m, 2H), 7.7 (m, 2H), 7.9 (d, 2H).

Mass spectrum: m/e 432 (M$^{+2}$).

Analysis calculated for C$_{25}$H$_{26}$N$_4$O$_3$•2HCl•H$_2$O: C, 57.58; H, 5.80, N, 10.75. Found: C, 58.03; H, 6.20; N, 10.78.

EXAMPLE 5

1-{7-[5-(3,5-Dimethylisoxazol-4-yl)-[1,2,4]oxadiazol-3-ylmethoxy]-naphthalen-1-yl}-4-methylpiperazine dihydrochloride hydrate Mp 222°–223° C.

$^1$H NMR (CDCl$_3$) δ 2.5 (s, 3H), 2.6 (s, 3H), 2.7 (bs, 4H) 2.8 (s, 3H), 3.2 (bs, 4H), 5.5 (s, 2H), 7.1 (d, 1H), 7.4 (m, 2H), 7.5 (d, 1H), 7.7 (d, 1H), 7.8 (d, 1H).

Mass spectrum: m/e 420 (M$^{+1}$).

Analysis calculated for C$_{23}$H$_{25}$N$_5$O$_3$•2HCl•H$_2$O: C, 54.12; H, 5.73, N, 13.72. Found: C, 53.75; H, 6.02; N, 13.66.

EXAMPLE 6

1-{7-[5-(2-MethoxyPhenyl)-[1,2,4]oxadiazol-3-ylmethoxyl]-naphthalen-1-yl}-4-methylpiperazine dihydrochloride hydrate Mp 186° C. (dec).

$^1$NMR (CDCl$_3$) δ 2.5 (s, 3H), 2.7 (bs, 4H), 3.2 (bs, 4H), 4.0 (s, 3H), 5.5 (s, 2H), 7.1 (m, 3H), 7.3 (m, 2H), 7.5 (m, 2H), 7.7 (d, 1H), 7.8 (d, 1H), 8.1 (bs, 1H).

Mass spectrum: m/e 432 (M$^{+2}$).

Analysis calculated for C$_{25}$H$_{26}$N$_4$O$_3$•2HCl•H$_2$O: C, 57.58; H, 5.80, N, 10.75. Found: C, 57.67; H, 5.95; N, 10.72.

EXAMPLE 7

1-{7-(5-Tert-butyl-[1,2,4 ]oxadiazol-3-ylmethoxy)-naphthalen-1-yl}-4-methylpiperazine hydrochloride dihydrate Mp 85° C. (dec).

$^1$H NMR (CDCl$_3$) δ 1.5 (s, 9H), 2.5 (s, 3H), 2.8 (bs, 4H), 3.2 (bs, 4H), 5.4 (s, 2H), 7.1 (d, 1H), 7.3 (m, 2H), 7.5 (d, 1H), 7.7 (d, 1H), 7.8 (d, 1H).

Mass spectrum: m/e 381 (M$^{+1}$).

Analysis calculated for C$_{22}$H$_{28}$N$_4$O$_2$•2HCl•2H$_2$O: C, 58.33; H, 7.34, N, 12.37. Found: C, 58.52; H, 7.18; N, 12.39.

EXAMPLE 8

1-Methyl-4-[7-(3-phenyl-[1,2,4]oxadiazol-5-ylmethoxy)-naphthalen-1-yl]-piperazine dihydrochloride hemihydrate Mp 160° C. (dec).

¹H NMR (CDCl₃) δ 2.4 (s, 3H), 2.7 (bs, 4H), 3.2 (bs, 4H), 5.6 (s, 2H), 7.1 (d, 1H), 7.3 (m, 2H), 7.5 (m, 4H), 7.6 (d, 1H), 7.8 (d, 1H), 8.2 (m, 2H).

Mass spectrum: m/e 401 (M$^{+1}$).

Analysis calculated for $C_{24}H_{24}N_4O_2 \cdot 2HCl \cdot 0.5H_2O$: C, 59.75; H, 5.64, N, 11.61. Found: C, 59.50; H, 5.70; N, 11.47.

EXAMPLE 9

1-{7-[5-(4-Methoxyphenyl)-[1,2,4]oxadiazol-3-ylmethoxy]-naphthalen-1-yl}-4-methylpiperazine dihydrochloride hydrate Mp 149° C. (dec).

¹HNMR (CDCl₃) δ 2.5 (s, 3H), 2.7 (bs, 4H), 3.2 (bs, 4H), 3.9 (s, 3H), 5.4 (s, 2H), 7.0 (d, 2H), 7.1 (d, 1H), 7.25 (m, 2H), 7.5 (d, 1H), 7.65 (d, 1H), 7.7 (d, 1H), 8.1 (d, 2H).

Mass spectrum: m/e 431 (M$^{+1}$).

Analysis calculated for $C_{25}H_{26}N_4O_3 \cdot 2HCl \cdot 1.5H_2O$: C, 56.60; H, 5.89, N, 10.56. Found: C, 56.30; H, 5.76; N, 10.28.

EXAMPLE 10

1-{7-[5-(4-Chlorophenyl)-[1,2,4]oxadiazol-3-ylmethoxy]-naphthalen-1-yl}-4-methylpiperazine dihydrochloride dihydrate Mp 186° C. (dec).

¹H NMR (CDCl₃) δ 2.5 (s, 3H), 2.7 (bs, 4H), 3.2 (bs, 4H), 5.4 (s, 2H), 7.05 (d, 1H), 7.25 (m, 2H), 7.5 (d, 3H), 7.65 (d, 1H), 7.7 (d, 2H), 8.1 (d, 2H).

Mass spectrum: m/e 435 (M$^{+1}$).

Analysis calculated for $C_{24}H_{23}N_4O_2 \cdot 2HCl \cdot 2H_2O$: C, 53.00; H, 5.37, N, 10.30. Found: C, 52.95; H, 5.05; N, 10.22.

EXAMPLE 11

1-{7-[5-(2,4-Dichlorobenzyl)-[1,2,4]oxadiazol-3-ylmethoxy]-naphthalen-1-yl}-4-methylpiperazine dihydrochloride hydrate Mp 90° C. (dec).

¹H NMR (CDCl₃) δ 2.5 (s, 3H), 2.7 (bs, 4H), 3.1 (bs, 4H), 5.3 (s, 2H), 5.4 (s, 2H), 6.8 (m, 1H), 7.1 (m, 2H), 7.3 (m, 2H), 7.4 (d, 1H), 7.5 (d, 1H), 7.6 (d, 1H), 7.7 (d, 1H).

Mass spectrum: m/e 499 (M$^{+NH_3}$).

Analysis calculated for $C_{25}H_{24}N_4O_3Cl_2 \cdot 2HCl \cdot H_2O$: C, 50.86; H, 4.78, N, 9.49. Found: C, 51.24; H, 4.70; N, 9.38.

EXAMPLE 12

1-{7-[3-(4-Chlorobenzyl)-[1,2,4]oxadiazol-5-ylmethoxyl- naphthalen-1-yl}-4-methylpiperazine dihydrochloride hemihydrate Mp 118° C. (dec)

¹H NMR (CDCl₃) δ 2.5 (s, 3H), 2.7 (bs, 4H), 3.1 (bs, 4H), 4.1 (s, 2H), 5.4 (s, 2H), 7.1 (d, 1H), 7.15–7.4 (m, 6H), 7.5 (d, 1H), 7.6 (d, 1H), 7.7 (d, 1H).

Mass spectrum: m/e 449 (M$^{+1}$).

Analysis calculated for $C_{25}H_{25}ClN_4O_2 \cdot 2HCl \cdot 0.5H_2O$: C, 56.56; H, 5.32, N, 10.55. Found: C, 56.89; H, 5.24; N, 10.56.

EXAMPLE 13

5-Chloro-2-[8-(4-methylpiperazin-1-yl)-naphthalen-2-yloxymethyl]-benzoxazole dihydrochloride Mp 195° C. (dec).

¹H NMR (CDCl₃,) δ 2.5 (s, 3H), 2.7 (bs, 4H), 3.1 (bs, 4H), 5.5 (s, 2H), 7.1 (d, 1H), 7.2–7.4 (m, 3H), 7.5 (m, 2H), 7.6–7.8 (m, 3H).

Mass spectrum: m/e 408 (M$^{+1}$).

Analysis calculated for $C_{23}H_{22}ClN_3O_2 \cdot 2HCl$: C, 57.45; H, 5.03, N, 8.74. Found: C, 57.11; H, 5.10; N, 8.69.

EXAMPLE 14

2-[8-(4-Methylpiperazin-1-yl)-naphthalen-2-yloxymethyl]-5-trifluoro-methylbenzothiazole dihydrochloride dihydrate Mp 179° C. (dec).

¹H NMR (CDCl₃) δ 2.5 (s, 3H), 2.6 (bs, 4H), 3.1 (bs, 4H), 5.2 (s, 2H), 7.0 (d, 1H), 7.2 (m, 2H), 7.5 (d, 1H), 7.6 (m, 2H), 7.7 (d, 1H), 8.0 (d, 1H), 8.3 (s, 1H).

Mass spectrum: m/e 458 (M$^{+1}$).

Analysis calculated for $C_{24}H_{22}F_3N_3OS \cdot 2HCl \cdot 2H_2O$: C, 46.10; H, 4.64, N, 6.45. Found: C, 46.56; H, 4.70; N, 6.55.

EXAMPLE 15

1-{7-[3-(4-Methoxyphenyl)-[1,2,4]oxadiazol-5-ylmethoxy]-naphthalen-1-yl}-4-methylpiperazine dihydrochloride hemihydrate Mp 184° C. (dec).

¹H NMR (CDCl₃) δ 2.4 (s, 3H), 2.7 (bs, 4H), 3.1 (bs, 4H), 3.8 (s, 3H), 5.5 (s, 2H), 7.0 (d, 2H), 7.1 (d, 1H), 7.2 (m, 2H), 7.5 (d, 1H), 7.6 (d, 1H), 7.7 (d, 1H), 8.0 (d, 2H).

Mass spectrum: m/e 431(M$^{+1}$).

Analysis calculated for $C_{25}H_{26}N_4O_3 \cdot 2HCl \cdot 0.5H_2O$: C, 58.59; H, 5.70, N, 10.93. Found: C, 58.68; H, 5.43; N, 10.72.

EXAMPLE 16

1-{7-[3-(2-Methoxyphenyl)-[1,2,4]oxadiazol-5-ylmethoxy]-naphthalen-1-yl}-4-methylpiperazine dihydrochloride hydrate Mp 206° C. (dec).

¹H NMR (CDCl₃) δ 2.4 (s, 3H), 2.7 (bs, 4H), 3.1 (bs, 4H), 3.9 (s, 3H), 5.5 (s, 2H), 7.0 (m, 3H), 7.2 (m, 2H), 7.4 (m, 2H), 7.6 (d, 1H), 7.7 (d, 1H), 8.2 (dd, 1H).

Mass spectrum: m/e 431 (M$^{30\ 1}$).

Analysis calculated for $C_{25}H_{26}N_4O_3 \cdot 2HCl \cdot H_2O$: C, 57.58; H, 5.80, N, 10.75. Found: C, 57.70; H, 5.48; N, 10.37.

EXAMPLE 17

1-{7-[3-(4-Chlorophenyl)-[1,2,4]oxadiazol-5-ylmethoxy]-naphthalen-1-yl}-4-methylpiperazine dihydrochloride Mp 231°–232° C. (dec).

¹H NMR (CDCl₃) δ 2.4 (s, 3H), 2.7 (bs, 4H), 3.2 (bs, 4H), 5.5 (s, 2H), 7.1 (d, 1H), 7.3 (m, 2H), 7.5 (m, 3H), 7.6 (d, 1H), 7.7 (d, 1H), 8.0 (d, 2H).

Mass spectrum: m/e 435 (M$^{+1}$).

Analysis calculated for $C_{24}H_{23}ClN_4O_2 \cdot 2HCl$: C, 56.76; H, 4.96, N, 11.03. Found: C, 56.36; H, 4.88; N, 10.78.

EXAMPLE 18

1-{7-[5-(2-Methoxyphenyl)-[1,2,4]oxadiazol-3-ylmethoxymethyl]-naphthalen-1-yl}-4-methylpiperazine dihydrochloride hydrate Mp 135° C. (dec).

¹H NMR (CDCl₃) δ 2.5 (s, 3H), 2.7 (bs, 4H), 3.2 (bs, 4H), 4.0 (s, 3H), 4.9 (s, 2H), 5.0 (s, 2H), 7.1 (m, 3H), 7.4 (t, 1H), 7.5 (m, 3H), 8.1 (dd, 1H ), 8.2 (s, 1H)

Mass spectrum: m/e 444 (M$^{+1}$).

Analysis calculated for $C_{26}H_{28}N_4O_3$•2HCl•1.5H₂O: C, 57.35; H, 6.11, N, 10.29. Found: C, 57.31; H, 6.20; N, 10.20.

EXAMPLE 19

1-(7-{1-[5-(4-Chlorophenyl)-[1,3,4]oxadiazol-2-yl]ethoxy}-naphthalen-1-yl}-4-methylpiperazine hydrochloride dihydrate Mp 65° C. (dec).

¹H NMR (CDCl₃,) δ 2.0 (d, 3H), 2.5 (s, 3H), 2.7 (bs, 4H) 3.2 (m, 4H), 5.9 (q, 1H), 7.1 (d, 1H), 7.2–7.4 (m, 2H), 7.5 (m, 3H), 7.7 (d, 1H), 7.75 (d, 1H ), 8.0 (d, 2H).

Mass spectrum: m/e 449 (M$^{+1}$).

Analysis calculated for $C_{25}H_{25}ClN_4O_2$•HCl•2H₂O: C, 57.58; H, 5.80, N, 10.74. Found: C, 58.15; H, 5.99; N, 10.52.

EXAMPLE 20

1-{7-[3-(2-Fluorophenyl)-[1,2,4]oxadiazol-5-ylmethoxy]-naphthalen-1-yl}-4-methylpiperazine dihydrochloride Mp 144° C.

¹H NMR (CDCl₃) δ 2.4 (s, 3H), 2.74 (bs, 4H), 3.09 (bs, 4H), 5.54 (s, 2H), 7.12 (dd, 1H), 7.21–7.35 (m, 4H), 7.51 (m, 2H), 7.60 (d, 1H), 7.79 (d, 1H), 8.08 (t, 1H).

Mass spectrum: m/e 419 (M$^{+1}$).

Analysis calculated for $C_{24}H_{23}FN_4O_2$•2HCl•1H₂O:C, 56.58;H, 5.34; N, 11.00. Found: C, 56.71; H, 5.40; N, 10.86.

EXAMPLE 21

5-Bromo-2-[8-(4-methylpiperazin-1-yl)-naphthalen-2-yloxymethyl]-benzooxazole dihydrochloride Mp 182° C. (dec).

¹H NMR (CDCl₃) δ 2.44 (s, 3H), 2.67 (bs, 4H), 3.07 (bs, 4H), 5.48 (s, 2H), 7.11 (dd, 1H), 7.29 (m, 2H), 7.41–7.52 (m, 3H), 7.66 (d, 1H), 7.77 (d, 1H), 7.89 (d, 1H).

Mass spectrum: m/e 452 (M$^{+1}$).

Analysis calculated for $C_{23}H_{22}BrN_3O_2$•2HCl•0.5H₂O: C, 51.70; H, 4.72; N, 7.86. Found: C, 52.07; H, 4.62; N, 7.74.

EXAMPLE 22

6-Fluoro-2-[8-(4-methylpiperazin-1-yl)-naphthalen-2-yloxymethyl]-benzooxazole dihydrochloride Mp 175° C. (dec).

¹H NMR (CDCl₃) δ 2.44 (s, 3H), 2.70 (bs, 4H), 3.08 (bs, 4H), 5.47 (s, 2H), 7.12 (m, 2H), 7.25–7.33 (m, 3H), 7.51 (d, 1H), 7.68 (m, 2H), 7.78 (d, 1H).

Mass spectrum: m/e 392 (M$^{+1}$).

EXAMPLE 23

6-Methoxy-2-[8-(4-methylpiperazin-1-yl)-naphthalen-2-yloxymethyl]-benzothiazole dihydrochloride Mp 191° C. (dec).

¹H NMR (CDCl₃) δ 2.42 (s, 3H), 2.63 (bs, 4H), 3.03 (bs, 4H), 3.87 (s, 3H), 5.61 (s, 2H), 7.10 (m, 2H), 7.25–7.33 (m, 3H), 7.50 (d, 1H), 7.63 (d, 1H), 7.78 (d, 1H), 7.93 (d, 1H).

Mass spectrum: m/e 420 (M$^{+1}$).

Analysis calculated for $C_{24}H_{25}N_3O_2S$•3HCl•3H₂O: C, 49.45; H, 5.88; N, 7.21. Found: C, 49.75; H, 5.83; N, 7.02.

EXAMPLE 24

2-[8-(4-Methylpiperazin-1-yl)-naphthalen-2-yloxyl]-pyrimidine

Mp 150–152° C. (dec).

¹H NMR (CDCl₃) δ 2.33 (s, 3H), 2.61 (bs, 4H), 3.08 (bs, 4H), 6.95 (t, 1H), 7.06 (d, 1H), 7.30 (m, 2H), 7.50 (d, 1H), 7.82 (d, 1H), 8.00 (s, 1H), 8.48 (d, 2H).

HRMS calculated for $C_{19}H_{20}N_4O$: 320.1642. Found: 320.16536.

EXAMPLE 25

2-[8-(4-Methylpiperazin-1-yl)-naphthalen-2-yloxyl]-5-trifluoromethyl-pyrimidine

Mp 84° 14 86° C. (dec).

¹H NMR (CDCl₃) δ 2.37 (s, 3H), 2.65 (bs, 4H), 3.12 (bs, 4H), 7.03 (d, 1H), 7.13 (d, 1H), 7.25 (dd, 1H), 7.40 (t, 1H), 7.56 (d, 1H), 7.88 (d, 1H), 7.95 (d, 1H), 8.45 (d, 1H).

Mass spectrum: m/e 388 (M⁺).

EXAMPLE 26

5-Fluoro-2-[8-(4-methylpiperazin-1-yl)-naphthalen-2-yloxy]-pyrimidine

¹H NMR (CDCl₃) δ 2.45 (s, 3H), 2.70 (bs, 4H), 3.15 (bs, 4H), 7.12 (d, 1H), 7.20 (dd, 1H), 7.30 (dd, 1H), 7.40 (t, 1H), 7.55 (t, 1H), 7.80–7.95 (m, 2H), 8.00 (d, 1H), 8.45 (s, 1H).

EXAMPLE 27

2-[8-(4-Methylpiperazin-1-yl)-naphthalen-2-yloxymethyl]-quinoline

¹H NMR (CDCl₃) δ 2.3 (s, 3H), 2.6 (bs, 4H), 3.2 (bs, 4H), 7.1 (m, 2H), 7.4 (m, 3H), 7.6 (m, 2H), 7.7 (m, 2H), 7.8 (d, 1H), 8.1 (d, 1H), 8.2 (d, 1H).

Mass spectrum: m/e 370 (M$^{+1}$).

HRMS calculated for $C_{24}H_{23}N_3O$: 369.1841. Found: 369.18087.

EXAMPLE 28

1-[7-(5-Chloropyridin-2-yloxy)-naphthalen-1-yl]-4-methyl-piperazine

¹H NMR (CDCl₃) δ 2.38 (s, 3H), 2.65 (bs, 4H), 3.12 (bs, 4H), 6.90 (d, 1H), 7.11 (d, 1H), 7.23 (dd, 1H), 7.37 (t, 1H), 7.55 (d, 1H), 7.65 (dd, 1H), 7.84 (d, 1H), 7.90 (d, 1H), 8.12 (d, 1H).

HRMS calculated for $C_{20}H_{20}ClN_3O$: 353.1295. Found: 353.11642.

EXAMPLE 29

1-[7-(5-Chlorothiophen-2-ylmethoxy)-naphthalen-1-yl]-4-methyl-piperazine mp 83° 14 85° C.

Mass spectrum: m/e 373 (M$^{+1}$).

¹H NMR (CDCl₃) δ 2.43 (s, 3H), 2.70 (bs, 4H), 3.10 (bs, 4H), 5.25 (s, 2H), 6.80 (d, 1H), 6.90 (d, 1H), 7.10 (d, 1H), 7.16 (dd, 1H), 7.27 (t, 1H), 7.50 (d, 1H), 7.58 (d, 1H) 7.75 (d, 1H).

EXAMPLE 30

2-[8-(4-Methylpiperazin-1-yl)-naphthalen-2-yloxy]-nicotinonitrile $^1$H NMR (CDCl$_3$) δ 2.37 (s, 3H), 2.65 (bs, 4H), 3.10 (bs, 4H), 7.05 (dd, 1H), 7.10 (d, 1H), 7.25 (dd, 1H), 7.37 (t, 1H), 7.55 (d, 1H), 7.85 (d, 1H), 7.98 (dd, 2H), 8.25 (dd, 1H).

HRMS calculated for C$_{21}$H$_{20}$N$_4$O: 344.1637. Found: 344.16176.

EXAMPLE 31

2-[8-(4-Methylpiperazin-1-yl)-naphthalen-2-yloxymethyl]-quinoline $^1$H NMR (CDCl$_3$) δ 2.25 (s, 3H), 2.35 (bs, 4H), 2.85 (bs, 4H), 5.55 (s, 2H), 7.0 (d, 1H), 7.2 (t, 1H), 7.3 (dd, 1H), 7.45 (m, 3H), 7.6 (d, 1H), 7.7 (m, 3H), 8.05 (d, 1H), 8.15 (d, 1H).

HRMS calculated for C$_{25}$H$_{25}$N$_3$O: 383.1992. Observed: 383.19964

EXAMPLE 32

2-[8-(1-Methylpiperidin-4-yl)-naphthalen-2-yloxy]-pyrimidine

Mp 134°–135° C.

$^1$H NMR (CDCl$_3$) δ 2.01 (m, 4H), 2.25 (m, 2H), 2.41 (s, 3H), 3.11 (bd, 2H), 3.21 (m, 1H), 7.07 (t, 1H), 7.35 (dd, 1H), 7.44 (d, 1H), 7.45 (s, 1H), 7.74 (m, 1H), 7.89 (d, 1H), 7.93 (d, 1H), 8.59 (d, 2H).

HRMS calculated for C$_{20}$H$_{21}$N$_3$O: 319.1680. Observed m/e: 319.1676.

Analysis calculated for C$_{20}$H$_{21}$N$_3$O•H$_2$O: C, 73.15; H, 6.75; N, 12.79. Found: C, 72.94; H, 6.78; N, 12.66.

EXAMPLE 33

1-Methyl-4-[7-(3-phenyl-[1,2,4]oxadiazol-5-ylmethoxy)-naphthalen-1-yl]-piperidine Mp 106°–108° C.

$^1$H NMR (CDCl$_3$) δ 1.85–2.03 (m, 4H), 2.22 (m, 2H), 2.36 (s, 3H), 3.02 (bd, 2H), 3.13 (m, 1H), 5.50 (s, 2H), 7.25–7.42 (m, 3H), 7.45–7.58 (m, 4H), 7.65 (d, 1H), 7.82 (d, 1H), 8.10 (dd, 2H).

HRMS calculated for C$_{25}$H$_{25}$N$_3$O$_2$: 399.4914. Observed m/e: 399.1965

Analysis calculated for C$_{25}$H$_{25}$N$_3$O$_2$•0.25H$_2$O: C, 74.33; H, 6.36; N, 10.40. Found: C, 74.23; H, 6.42; N, 10.49.

EXAMPLE 34

1-Methyl-4-[7-(pyridin-2-ylmethoxy)-naphthalen-1-yl]-piperazine $^1$H NMR (CDCl$_3$) δ 2.38 (s, 3H), 2.60 (bs, 4H), 2.99 (bs, 4H), 5.35 (s, 2H), 7.03 (d, 1H), 7.23 (m, 3H), 7.43–7.53 (m, 3H), 7.63 (m, 1H), 7.71 (d, 1H), 8.59 (m, 1H).

HRMS calculated for C$_{21}$H$_{23}$N$_3$O: 333.1841. Observed m/e: 333.18425.

EXAMPLE 35

1-Methyl-4-[7-(3-pyridin-3-ylpropoxy)-naphthalen-1-yl]-piperazine $^1$H NMR (CDCl$_3$) δ 2.2 (q, 2H), 2.4 (s, 3H), 2.75 (bs, 4H), 2.9 (t, 2H), 3.15 (bs, 4H), 4.1 (t, 2H), 7.05–7.30 (m, 4H), 7.5 (m, 3H), 7.7 (d, 1H), 8.45 (dd, 1H), 8.52 (d, 1H).

HRMS calculated for C$_{23}$H$_{27}$N$_3$O: 361.2148. Observed m/e: 361.21118.

EXAMPLE 36

1-{7-[2-(4-Chlorophenyl)-thiazol-4-ylmethoxy]-naphthalen-1-yl}-4-methyl-piperazine $^1$H NMR (CDCl$_3$) δ 2.25 (s, 3H), 2.6 (bs, 4H), 3.05 (bs, 4H), 5.4 (s, 2H), 7.05 (d, 1H), 7.25 (m, 3H), 7.35 (m, 2H), 7.5 (d, 1H), 7.55 (d, 1H), 7.75 (d, 1H), 7.85 (d, 2H).

HRMS calculated for C$_{25}$H$_{24}$ClN$_3$OS: 449.1407. Observed m/e: 449.13387.

EXAMPLE 37

4-{7-[5-(3,5-Dimethylisoxazol-4-yl)-[1,2,4]oxadiazol-3-ylmethoxy]-naphthalen-1-yl}-1-methylpiperidine Mp 84°–86° C.

$^1$H NMR (CDCl$_3$) δ 1.80–2.00 (m, 4H), 2.23 (dt, 2H), 2.39 (s, 3H), 2.59 (s, 3H), 2.81 (s, 3H), 3.06 (bd, 2H), 3.18 (m, 1H), 5.40 (s, 2H), 7.26–7.32 (m, 1H), 7.36 (d, 1H), 7.41 (dd, 1H), 7.56 (d, 1H), 7.67 (d, 1H), 7.82 (d, 1H).

HRMS calculated for C$_{24}$H$_{26}$N$_4$O$_3$: 418.1999. Observed m/e: 418.1996.

EXAMPLE 38

7-Chloro-2-[8-(4-methylpiperazin-1-yl)-naphthalen-2-yloxymethyl]-quinoline

Mp 246°–247° C. (dec.)

$^1$H NMR (CDCl$_3$) δ 2.30 (s, 3H), 2.40 (bs, 4H), 2.86 (bs, 4H), 5.52 (s, 2H), 7.01 (d, 1H), 7.25 (m, 2H), 7.45 (m, 3H), 7.63 (m, 2H), 7.73 (d, 1H), 8.02 (d, 1H), 8.13 (d, 1H).

$^{13}$H NMR (CDCl$_3$) ppm: 46.1, 52.2, 55.5, 71.1, 103.9, 115.4, 118.7, 119.1, 123.2, 123.9, 125.8, 127.5, 128.2, 128.9, 129.8, 130.2, 130.3, 135.6, 136.6, 148.0, 148.6, 155.9, 159.7.

Mass spectrum: m/e 418 (M$^{+1}$).

EXAMPLE 39

6-Chloro-5-{2-[8-(4-methylpiperazin-1-yl)-naphthalen-2-yloxy]-ethyl}-1,3-dihydro-indol-2-one Mp 93° C. (dec.).

$^1$H NMR (CDCl$_3$,) δ 2.4 (s, 3H), 2.75 (bs, 4H), 3.15 (bs, 4H), 3.25 (t, 2H), 3.50 (s, 2H), 4.35 (t, 2H), 6.9 (s, 1H), 7.1 (t, 2H), 7.25 (t, 2H), 7.50 (d, 1H), 7.55 (m, 1H), 7.70 (d, 1H), 9.40 (s, 1H).

HRMS calculated for C$_{25}$H$_{26}$ClN$_3$O$_2$: 435.1714. Found: 435.17042.

EXAMPLE 40

3-[8-(4-Methylpiperazin-1-yl)-naphthalen-2-yloxy-]-6-phenylpyridazine

Mp 158°–160° C.

$^1$H NMR (CDCl$_3$) δ 2.35 (s, 3H), 2.64 (bs, 4H), 3.12 (bs, 4H), 7.11 (d, 1H), 7.23 (t, 1H), 7.33–7.46 (m, 5H), 7.55 (d, 1H), 7.85 (m, 2H), 8.00 (m, 3H).

Mass spectrum: m/e 397 (M$^{+1}$).

According to the methods of U.S. patent application Ser. No. 08/032,042 now abandoned and PCT Application No. PCT/US 94/01206. The following examples were prepared.

EXAMPLE 41

8-(4-Methylpiperazin-1-yl)-naphthalene-2-carboxylic acid [1-(4-chlorophenyl)ethyl]-amide Mp 152.5°–153° C.

$^1$H NMR (CDCl$_3$) δ 1.65 (d, 3H), 2.45 (s, 3H), 2.75 (bs, 4H), 3.20 (bs, 4H), 5.38 (m, 1H), 6.45 (d, 1H), 7.15 (dd, 1H), 7.27 (s, 1H), 7.40 (m, 3H), 7.50 (t, 1H), 7.60 (d, 1H), 7.75 (dd, 1H), 7.90 (d, 1H), 8.75 (s, 1H).

Mass spectrum: m/e 407 (M$^+$).

EXAMPLE 42

8-(4-Methylpiperazin-1-yl)-naphthalene-2-carboxylic acid [3-(4-chlorophenyl)propyl]-amide Mp 121.5°–123° C.

$^1$H NMR (CDCl$_3$) δ 2.05 (m, 2H), 2.45 (s, 2H), 2.75 (m, 6H), 3.20 (bs, 4H), 3.55 (m, 2H), 6.35 (bs, 1H), 7.10–7.35 (m, 5H), 7.48 (m, 1H), 7.55 (d, 1H), 7.68 (m, 1H), 7.85 (dd, 1H), 8.68 (bs, 1H).

Mass spectrum: m/e 421 (M$^+$).

EXAMPLE 43

8-(Piperazin-1-yl)-naphthalene-2-carboxylic acid 4-chlorobenzamide $^1$H NMR (CDCl$_3$) δ 1.78 (s, 1H), 3.05 (m, 9H), 4.60 (d, 2H), 6.85 (t, 1H), 7.07 (dd, 1H), 7.23 (m, 3H), 7.45 (m, 2H), 7.74 (m, 2H), 8.65 (s, 1H).

EXAMPLE 44

8-(4-Methylpiperazin-1-yl)-naphthalene-2-carboxylic acid (4-chloro-benzyl)-methylamide dihydrochloride $^1$H NMR (CDCl$_3$,free base) δ 2.7 (s, 1H), 2.95–3.80 (m, 13H), 4.07 (d, 1H), 4.7 (d, 1H), 7.2–7.65 (m, 7H), 7.75 (d, 1H), 7.95 (d, 1H), 8.25 (d, 1H).

Mass spectrum: m/e 407 (M$^+$).

EXAMPLE 45

8-(4-Methylpiperazin-1-yl)-naphthalene-2-carboxylic acid [2-(4-chlorophenyl)ethyl]-amide Mp 122° 14 123° C.

$^1$H NMR (CDCl$_3$) δ 2.45 (s, 3H), 2.77 (bs, 4H), 2.95 (t, 2H), 3.12 (bs, 4H), 3.32 (m, 1H), 3.68 (t, 2H), 7.17 (dd, 1H), 7.30 (m, 4H), 7.50 (t, 1H), 7.60 (d, 1H), 7.80 (dd, 1H), 7.90 (d, 1H), 8.62 (d, 1H).

Mass spectrum: m/e 408 (M$^{+1}$).

EXAMPLE 46

8-(4-Methylpiperazin-1-yl)-naphthalene-2-carboxylic acid pyrimidin-4-ylamide $^1$H NMR (CDCl$_3$) δ 2.36 (s, 3H), 2.70 (bs, 4H), 3.10 (bs, 4H), 7.15 (dd, 1H), 7.55 (q+t, 2H), 7.91 (d, 1H), 8.41 (dd, 1H), 8.65 (d, 1H), 8.73 (d, 1H), 8.82 (s, 1H), 9.48 (s, 1H).

HRMS calculated for C$_{20}$H$_{21}$NO$_5$O: 347.1742. Found: 347.16974.

The compounds of Examples 47–50 were prepared from the intermediates of Preparation 5.

EXAMPLE 47

1-(1-Methylpiperidin-4-yl)-7-naphthalene carboxylic acid 3-phenylpropylamide

A mixture of 1-(1-methylpiperidin-4-yl)-7-trifluoromethanesulfonyloxynaphthalene (0.25 g, 0.67 mmol), triethylamine (0.373 mL, 2.68 mmol), 3-phenylpropylamine (0.286 mL, 2.01 mmol), and bis-(triphenylphosphine)palladium chloride (0.025 g, 0.033 mmol) was blanketed with an atmosphere of carbon monoxide (balloon) and heated to 105° C. for 16 h. The reaction was diluted with ethyl acetate and filtered through celite. The filtrate was washed with water and brine, dried and concentrated. The residue was flash chromatographed on silica gel (1×3 inches packed with 75% ethyl acetate/hexane). Elution proceeded as follows: 75% ethyl acetate/hexane, 150 mL, nil; ethyl acetate, 150 mL, nil; 2% methanol/1% triethylamine/ethyl acetate, 200 mL and 2% methanol/1% triethylamine/ethyl acetate, 100 mL, 0.21 g of an oil. Bulb to bulb distillation removed impurities (pot temperature up to 120° C., 1 mm mercury (Hg)). The pot residue was pure product and weighed 0.190 g (73%). The 1-(1-methylpiperidin-4-yl)-7-naphthalene carboxylic acid 3-phenylpropyl amide obtained in this manner solidified on standing and had mp 47°–50° C.; 1H NMR (250 MHz, CDCl$_3$) δ 8.67 (s, 1H), 7.86 (d, J=8.5 Hz, 1H), 7.73 (d, J=6.5 Hz, 1H), 7.61–7.43 (m, 3H), 7.36–7.18 (m, 5H), 6.33 (br s, 1H), 3.58 (q, J=6.5 Hz, 2H), 3.42 (sym m, 1H), 3.05 (br d, J=11.5 Hz, 2H), 2.77 (t, J=7.5 Hz, 2H), 2.38 (s, 3H), 2.27 (sym m, 2H), 2.10–1.88 (m, 6H). Analysis calculated for C$_{26}$H$_{30}$N$_2$O•0.75 H$_2$O: C, 78.06; H, 7.94; N, 7.00. Found: C, 77.92; H, 7.91; N, 6.70.

EXAMPLE 48

1-(1-Methylpiperidin-4-yl)-7-naphthalene carboxylic acid 3-(4-chlorophenyl)propyl amide A mixture of 1-(1-methylpiperidin-4-yl)-7-trifluoromethanesulfonyloxynaphthalene (0.25 g, 0.67 mmol), triethylamine (0.373 mL, 2.68 mmol), 3-(4-chlorophenyl)propylamine (0.341 mL, 2.01 mmol), and bis(triphenylphosphine)palladium chloride (0.025 g, 0.033 mmol) was blanketed with an atmosphere of carbon monoxide (balloon) and heated to 105° C. for 16 hours (h) . The reaction was diluted with ethyl acetate and filtered through celite. The filtrate was washed with water and brine, dried and concentrated. The residue was flash chromatographed on silica gel (1×3 inches packed with 75% ethyl acetate/hexane). Elution proceeded as follows: 75% ethyl acetate/hexane, 150 mL, nil; ethyl acetate, 150 mL, nil; 2% methanol/1% triethylamine/ethyl acetate, 200 mL and 2% methanol/1% triethylamine/ethyl acetate, 150 mL, 0.196 g of a yellow-oil which slowly crystallized. This material was recrystallized from chloroform/ether to give 0.064 g (23%) of 1-(1-methylpiperidin-4-yl)-7-naphthalene carboxylic acid 3-(4-chlorophenyl)propyl amide as white crystals which had mp 132°–133.5° C.; $^1$H NMR (250 MHz, CDCl$_3$) δ 8.66 (s, 1H), 7.87 (d, J=8.5 Hz, 1H), 7.72 (d, J=7.5 Hz, 1H), 7.58–7.46 (m, 3H), 7.27–7.23 (m, 2H partially obscured by the NMR solvent), 7.15 (long range coupled d, J=8.5 Hz, 2H), 6.23 (br t, 1H), 3.55 (q, J=6.5 Hz, 2H), 3.39 (sym m, 1H), 3.02 (br d, J=12 Hz, 2H), 2.72 (t, J=7.5 Hz, 2H), 2.36 (s, 3H), 2.23 (sym m, 2H), 2.04–1.89 (m, 6H). Analysis calculated for C$_{26}$H$_{29}$ClN$_2$O•0.25 H$_2$O: C, 73.40; H, 6.99; N, 6.58. Found: C, 73.30; H, 7.12; N, 6.56.

EXAMPLE 49

1-(1-Methylpiperidin-4-yl)-7-(pyrimid-5-yl)-naphthalene

A mixture of 1-(1-methylpiperidin-4-yl)-7-trifluoromethanesulfonyloxynaphthalene (0.304 g, 0.819 mmol), 5-trimethylstannylpyrimidine (0.220 g, 0.905 mmol), triethylamine (0.55 mL, 3.95 mmol), lithium chloride (0.107 g, 2.53 mmol), bis(triphenylphosphine) palladium chloride (0.029 g, 0.041 mmol), and butylated hydroxytoluene (BHT, approx. 0.01 g, antioxidant) in dimethylformamide (15 mL) was heated to 115° C. for 1 hour. The reaction was cooled and diluted with ethyl acetate. The mixture was extracted with a mixture of 1N lithium chloride (25 mL) and 1N sodium hydroxide (3 mL), 1N lithium chloride and brine. The organic phase was dried over calcium sulfate and concentrated. The residue was flash chromatographed on silica gel (1×2.5 inches packed with 75% ethyl acetate/hexane). Elution proceeded as follows: 75% ethyl acetate/hexane, 225 mL, nil; ethyl acetate, 200 mL, nil; 1% methanol/ethyl acetate, 200 mL, nil; 5% methanol/ethyl acetate, 300 mL, nil; and 7% methanol/1% triethylamine/ethyl acetate, 250 mL, 0.130 g (52%) of 1-(1-methylpiperidin-4-yl)-7-pyrimid-5-yl-naphthalene as a tan foam. A sample triturated with ether afforded white crystals which had: Mp 121.5°–123° C.; $^1$H NMR (250 MHz, CDCl$_3$) δ 9.27 (s, 1H), 9.08 (s, 2H), 8.26 (s, 1 H), 8.03 (d, J=8.5 Hz, 1H), 7.78 (dd, J=3, 6.5 Hz, 1H), 7.69 (dd, J=1.5, 8.5 Hz, 1H), 7.57–7.50 (m, 2H), 3.36 (sym m, 1H), 3.09 (br d, J=12 Hz, 2H), 2.40 (s, 3H), 2.28 (sym m, 2H), 2.06–1.90 (m, 4H). Analysis calculated for C$_{20}$H$_{21}$N$_3$: C, 79.17; H, 6.98;N, 13.85. Found: C, 78.46; H, 7.14; N, 13.89. HRMS m/e 303.1731. Observed m/e 303.1700.

EXAMPLE 50

1-(1-Methylpiperidin-4-yl)-7-(3-methoxyphenyl) naphthalene

A mixture of 1-(1-methylpiperidin-4-yl)-7-trifluoromethanesulfonyloxynaphthalene (0.264 g, 0.712 mmol), 3-trimethylstannylanisole (0.212 g, 0.783 mmol), triethylamine (0.476 mL, 3.42 mmol), lithium chloride (0.093 g, 2.21 mmol), bis-(triphenylphosphine)palladium chloride (0.025 g, 0.036 mmol), and butylated hydroxytoluene (BHT, ~0.01 g, antioxidant) in dimethylformamide (12.5 mL) was heated to 115° C. for 2 h. The reaction was cooled and diluted with ethyl acetate. The mixture was extracted with a mixture of 1N lithium chloride (25 mL) and 1N sodium hydroxide (3 mL), 1N lithium chloride and brine. The organic phase was dried over calcium sulfate and concentrated. The residue was flash chromatographed on silica gel (1×2.5 inches packed with 75% ethyl acetate/hexane). Elution proceeded as follows: 75% ethyl acetate/hexane, 300 mL, nil; ethyl acetate, 200 mL, 0.104 g of a yellow oil. The oil was distilled (bulb to bulb) collecting three fractions: 25°–143° C. (1 mm Hg), 0.037 g identified as 1-(1-methylpiperidin-4-yl)-7-methylnaphthalene; 143°–168° C. (1 mm Hg), 0.008 g of a mixed fraction; 168°–200° C., 0.049 g (21%) of 1-(1-methylpiperidin-4-yl)-7-(3-methoxyphenyl)naphthalene as a clear yellow oil which had $^1$H NMR (250 MHz, CDCl$_3$) δ 8.26 (s, 1H), 7.94 (d, J=8.5 Hz, 1H), 7.77–7.70 (m, 2H), 7.47–7.40 (m, 3H), 7.32 (d, J=7.5 Hz, 1H), 7.27–7.25 m, 1 H partially obscured by the $^1$H NMR solvent), 6.96 (dd, J=2.5, 8.5 Hz, 1H), 3.92 (s, 3H), 3.38 (sym m, 1H), 3.07 (br d, J=11.5 Hz, 2H), 2.39 (s, 3H), 2.25 (dt, J=3.5, 11 Hz, 2H), 2.08–1.89 (m, 4H). The product was dissolved in chloroform and HCl (gas) was bubbled into the solution. The solvent was removed and the residue was triturated with ether to afford the hydrochloride salt which had: mp 212°–214° C. Analysis calculated for C$_{23}$H$_{25}$N·HCl: C, 75.09; H, 7.12; N, 3.81. Found: C, 75.22; H, 7.44; N, 4.19.

EXAMPLE 51

1-(1-Methylpiperidin-4-yl)-7-(pyrid-3-yl)-naphthalene

A mixture of 1-(1-methylpiperidin-4-yl)-7-trifluoromethanesulfonyloxynaphthalene (0.250 g, 0.67 mmol), 3-trimethylstannylpyridine (0.227 g, 0.94 mmol), triethylamine (0.448 mL, 3.22 mmol), lithium chloride (0.093 g, 2.21 mmol), bis-(triphenylphosphine)palladium chloride (0.025 g, 0.036 mmol), and butylated hydroxytoluene (BHT, ~0.01 g, antioxidant) in dimethylformamide (12.5 mL) was heated to 115° C. for 2.5 h. The reaction was cooled and diluted with ethyl acetate. The mixture was extracted with a mixture of 1N lithium chloride (25 mL) and 1N sodium hydroxide (3 mL), 1N lithium chloride and brine. The organic phase was dried over calcium sulfate and concentrated. The residue was flash chromatographed on silica gel (1×3 inches packed with 75% ethyl acetate/hexane). Elution proceeded as follows: 75% ethyl acetate/hexane, 300 mL, nil; ethyl acetate, 200 mL, nil; 4% methanol/1% triethylamine/ethyl acetate, 300 mL, 0.091 g (45%) of 1-(1-methylpiperidin-4-yl)-7-(pyrid-3-yl) naphthalene as a brown oil. The product was further purified by bulb to bulb distillation with the product obtained at 220° C. (1 mm Hg) as an orange oil which had: $^1$H NMR (250 MHz, CDCl$_3$) δ 8.99 (m, 1H), 8.66 (dd, J=1.5, 5 Hz, 1H), 8.26 (s, 1H), 8.06–7.97 (m, 3H), 7.81–7.76 (m, 1H), 7.70 (dd, J=1.5, 8.5 Hz, 1H), 7.52–7.40 (m, 3H), 3.38 (sym m, 1H), 3.10 (br d, J=11.5 Hz, 2H), 2.41 (s, 3H), 2.28 (sym m, 2H), 2.10–1.93 (m, 4H). The product was dissolved in chloroform and HCl (gas) was bubbled into the solution. The solvent was removed and the residue was triturated with ether to obtain 0.08 g of the hydrochloride salt as an amorphous solid which had: melting range 130°–160° C. Analysis calculated for C$_{21}$H$_{22}$N$_2$·2 HCl·2.5 H$_2$O: C, 60.00; H, 6.95; N, 6.66. Found: C, 59.49; H, 6.85; N, 6.35.

EXAMPLE 52

General Procedure for the Synthesis of 1-(4-Methylpiperazin-1-yl)-7-(1,2,4-oxadiaz-5-yl) naphthalene To a stirred solution of sodium (2.5 equivalents) in absolute methanol (25 mL per gram sodium) at 0° C. was added hydroxylamine hydrochloride (2.5 equivalents) as a solid, and the resulting mixture was stirred at room temperature under nitrogen for 30 minutes. Then, the appropriate nitrile (1.0 equivalent) was added, and the resulting reaction mixture was heated at reflux overnight (16 hours). The reaction mixture was then cooled, filtered through Celite®, and the filtrate was evaporated under reduced pressure to afford the corresponding crude amidoxime which was used immediately and directly in the next step.

To a stirred solution of the crude amidoxime (2.0 equivalents) in anhydrous tetrahydrofuran (20 mL per gram of amidoxime) was added sodium hydride (2.2 equivalents), and the resulting reaction solution was heated at reflux under nitrogen for 30 minutes. The reaction solution was cooled, and a solution of benzyl 1-(4-methylpiperazin-1-yl) naphthalene-7-carboxylate (1.0 equivalent) in anhydrous tetrahydrofuran [10 mL per gram of benzyl 1-(4-methylpiperazin-1-yl)naphthalene-7-carboxylate] was added. The resulting reaction solution was then heated at reflux under nitrogen for two hours. The resulting reaction solution was evaporated under reduced pressure, and the residue was chromatographed using silica gel (50 g per gram residue) and elution with an appropriate solvent system to afford the corresponding 1-(4-methylpiperazin-1-yl)-7-(1,2,4-oxadiaz-5-yl)naphthalene.

Using this general procedure, the following compounds were prepared:

A. 7-(3-(4-Chlorophenylmethyl)-1,2,4-oxadiaz-5-yl)-1-(4-methylpiperazin-1-yl)-naphthalene Sodium (5.6 g, 0.25 mol), hydroxylamine hydrochloride (17.3 g, 0.25 mol), and (4-chlorophenyl)acetonitrile (15.1 g, 0.10 mol) and methanol (150 mL) were used to prepare (4-chlorophenyl)acetamidoxime (18.5 g, 0.10 mol, 100%) as described above.

(4-Chlorophenyl)acetamidoxime (0.374 g, 2.00 mmol), sodium hydride (60% dispersion in oil, 0.093 g, 2.3 mmol), benzyl 1-(4-methylpiperazin-1-yl)naphthalene-7-carboxylate (0.360 g, 1.00 mmol), and anhydrous tetrahydrofuran (12 mL total) were to used form the title compound as described above. Chromatographic purification using elution with 10% methanol in ethyl acetate afforded the title compound (0.105 g, 0.25 mmol, 25%) as a off-white foam: $^{13}$C NMR (acetone-$d_6$) δ 176.7, 170.8, 150.0, 137.4, 135.8, 133.1, 131.6, 130.6, 129.7, 129.3, 128.9, 125.2, 124.9, 124.8, 121.9, 117.9, 55.2, 51.3, 44.2, 31.9; LRMS (m/z, relative intensity) 420 ([M$^+$ with $^{37}$Cl], 36), 419 (46), 418 ([M$^+$ with $^{35}$Cl], 100), 403 (14), 151 (86), 113 (77); HRMS calculated for $C_{24}H_{23}ClN_4O$ 418.1555, found 418.1543.

B. 1-(4-Methylpiperazin-1-yl)-7-(3-(pyrid-4-ylmethyl)-1,2,4-oxadiaz-5-yl)naphthalene Sodium (0.253 g, 11.5 mmol), hydroxylamine hydrochloride (0.570 g, 8.20 mmol), and (4-pyridyl)acetonitrile hydrochloride (0.500 g, 3.2 mmol) and methanol (5 mL) were used to prepare (4-pyridyl)acetamidoxime (0.580 g, >100%) as described above.

(4-Pyridyl)acetamidoxime (0.580 g, assumed 3.2 mmol), sodium hydride (60% dispersion in oil, 0.160 g, 4.0 mmol), benzyl 1-(4-methylpiperazin-1-yl)naphthalene-7-carboxylate (0.600 g, 1.66 mmol), and anhydrous tetrahydrofuran (16 mL total) were used to form the title compound as described above. Chromatographic purification using elution with 3% methanol in methylene chloride afforded the title compound (0.075 g, 0.19 mmol, 12%) as a off-white foam: $^{13}$C NMR (CD$_3$OD) δ 176.4, 168.8, 150.5, 149.0, 148.9, 146.4, 136.8, 129.4, 128.7, 128.1, 124.7, 124.6, 123.2, 122.5, 120.2, 116.1, 55.0, 52.4, 44.8, 30.9; FAB LRMS (m/z, relative intensity) 387 (32), 386 (M$^+$, 100). Anal. calcd for $C_{23}H_{23}N_5O$ 0.33 NH$_2$OH [hydroxylamine]: C, 69.70; H, 6.10; N, 18.84. Found: 69.89; H, 6.00; N, 18.94.

C. 1-(4-Methylpiperazin-1-yl)-7-(3-(pyrid-3-ylmethyl)-1,2,4-oxadiaz-5-yl)naphthalene Sodium (0.183 g, 7.96 mmol), hydroxylamine hydrochloride (0.570 g, 8.20 mmol), and (3-pyridyl)acetonitrile (0.375 g, 3.17 mmol) and methanol (5 mL) were used to prepare (3-pyridyl)acetamidoxime (0.50 g, >100%) as described above.

(3-Pyridyl)acetamidoxime (0.50 g, assumed 3.17 mmol), sodium hydride (60% dispersion in oil, 0.282 g, 7.0 mmol), benzyl 1-(4-methylpiperazin-1-yl)naphthalene-7-carboxylate (0.576 g, 1.60 mmol), and anhydrous tetrahydrofuran (16 mL total) were used to form the title compound as described above. Chromatographic purification using elution with 6% methanol in methylene chloride afforded the title compound (0.160 g, 0.42 mmol, 26%) as a off-white foam: $^{13}$C NMR (CD$_3$OD) δ 176.4, 169.5, 150.5, 149.2, 147.4, 137.6, 136.8, 132.5, 129.4, 128.7, 128.1, 124.5, 123.9, 123.2, 123.2, 120.3, 116.1, 55.0, 52.4, 44.7, 28.9; LRMS (m/z, relative intensity) 386 (18), 385 (M$^+$, 61), 370 (63), 342 (100), 315 (29), 287 (22), 71 (59); HRMS calculated for $C_{23}H_{23}N_5O$ 385.1898, found 385.1906. Anal. calcd for $C_{23}H_{23}N_5O$ 0.5 H$_2$O: C, 70.03; H, 6.13; N, 17.75. Found: C, 69.67; H, 6.12; N, 17.71.

D. 1-(4-Methylpiperazin-1-yl)-7-(3-(pyrid-2-ylmethyl)-1,2,4-oxadiaz-5-yl)naphthalene Sodium (0.183 g, 7.96 mmol), hydroxylamine hydrochloride (0.570 g, 8.20 mmol), and (2-pyridyl)acetonitrile (0.375 g, 3.17 mmol) and methanol (5 mL) were used to prepare (2-pyridyl)acetamidoxime (0.55 g, >100%) as described above.

(2-Pyridyl)acetamidoxime (0.55 g, assumed 3.17 mmol), sodium hydride (60% dispersion in oil, 0.282 g, 7.0 mmol), benzyl 1-(4-methylpiperazin-1-yl)naphthalene-7-carboxylate (0.576 g, 1.60 mmol), and anhydrous tetrahydrofuran (16 mL total) were used to form the title compound as described above. Chromatographic purification using elution with 6% methanol in methylene chloride afforded the title compound (0.122 g, 0.32 mmol, 20%) as a off-white foam: LRMS (m/z, relative intensity) 386 (18), 385 (M$^+$, 100), 370 (27), 182 (59), 154 (45); HRMS calculated for $C_{23}H_{23}N_5O$ 385.1898, found 385.1910.

E. 7-(3-(4-Chlorophenyl)-1,2,4-oxadiaz-5-yl)-1-(4-methylpiperazin-1-yl)naphthalene Sodium (0.24 g, 10.4 mmol), hydroxylamine hydrochloride (0.70 g, 10 mmol), and 4-chlorobenzonitrile (0.548 g, 3.98 mmol) and methanol (10 mL) were used to prepare (4-chlorophenyl)amidoxime (0.70 g, 100%) as described above.

(4-Chlorophenyl)amidoxime (0.70 g, assumed 3.97 mmol), sodium hydride (60% dispersion in oil, 0.176 g, 4.4 mmol), benzyl 1-(4-methylpiperazin-1-yl)naphthalene-7-carboxylate (0.720 g, 2.0 mmol), and anhydrous tetrahydrofuran (25 mL total) were used to form the title compound as described above. Chromatographic purification using elution with 6% methanol in methylene chloride afforded the title compound (0.164 g, 0.41 mmol, 20%) as a off-white foam: $^{13}$C NMR (CDCl$_3$) δ 176.4, 168.2, 151.0, 137.5, 136.8, 129.5, 129.2, 128.9, 128.5, 125.8, 125.3, 124.0, 123.2, 120.7, 116.1, 55.5, 53.2, 46.2; LRMS (m/z, relative intensity) 406 ([M$^+$ with $^{37}$Cl], 52), 405 (45), 404 ([M$^+$ with $^{35}$Cl], 100), 319 (34), 70 (75); HRMS calculated for $C_{23}H_{21}N_4O$ 404.1399, found 404.1386. Anal. calcd for $C_{23}H_{21}N_4O$: C, 68.23; H, 5.23; N, 13.84. Found: C, 68.12; H, 5.31; N, 13.96.

F. 7-(3-Methyl-1,2,4-oxadiaz-5-yl)-1-(4-methylpiperazin-1-yl)naphthalene

Sodium (0.24 g, 10.4 mmol), hydroxylamine hydrochloride (0.70 g, 10 mmol), and acetonitrile (1.2 mL, 23.0 mmol) and methanol (10 mL) were used to prepare acetamidoxime (0.80 g, >100%) as described above.

Acetamidoxime (0.80 g, assumed 10 mmol), sodium hydride (60% dispersion in oil, 0.174 g, 4.4 mmol), benzyl 1-(4-methylpiperazin-1-yl)naphthalene-7-carboxylate (0.760 g, 2.1 mmol), and anhydrous tetrahydrofuran (25 mL total) were used to form the title compound as described above. Chromatographic purification using elution with 6% methanol in methylene chloride afforded the title compound (0.120 g, 0.39 mmol, 19%) as a off-white amorphous solid: $^{13}$C NMR (CD$_3$OD) δ 177.2, 169.1, 151.9, 138.1, 130.8, 130.0, 129.5, 125.8, 124.6, 124.5, 121.8, 117.4, 56.4, 53.9, 46.2, 11.5; LRMS (m/z, relative intensity) 309 (17), 308 (M$^+$, 100), 293 (11), 223 (20), 71 (39); HRMS calculated for $C_{18}H_{20}N_4O$: 308.1633, found 308.1617. Anal. calcd for $C_{18}H_{20}N_4O$•0.25 H$_2$O: C, 69.10; H, 6.60; N, 17.91. Found: C, 69.24; H, 6.55; N, 17.79.

G. 7-(3-(4-Chlorophenoxymethyl)-1,2,4-oxadiaz-5-yl)-1-(4-methylpiperazin-1-yl)naphthalene Sodium (0.24 g, 10.4 mmol), hydroxylamine hydrochloride (0.72 g, 10 mmol), and (4-chlorophenoxy)acetonitrile (0.67 g, 4.0 mmol) and methanol (5 mL) were used to prepare (4-chlorophenoxy)acetamidoxime (0.85 g, >100%) as described above.

(4-chlorophenoxy)acetamidoxime (0.85 g, assumed 4.0 mmol), sodium hydride (60% dispersion in oil, 0.190 g, 4.7 mmol), benzyl 1-(4-methylpiperazin-1-yl)naphthalene-7-carboxylate (0.720 g, 2.0 mmol), and anhydrous tetrahydrofuran (25 mL total) were used to form the title compound as described above. Chromatographic purification using elution with ethyl acetate/methanol/triethylamine [65:1:1] afforded the title compound (0.238 g, 0.55 mmol, 27%) as a off-white foam: $^{13}$C NMR (CDCl$_3$) δ 177.0, 167.2, 156.6, 151.0, 136.8, 129.6, 129.5, 128.9, 128.4, 126.8, 125.5, 123.9, 123.3, 120.3, 116.4, 116.1, 61.6, 55.4, 53.2, 46.1; LRMS (m/z, relative intensity) 436 ([M$^+$ with $^{37}$Cl], 17), 435 (12), 434 ([M$^+$ with $^{35}$Cl],100), 71 (97), 70 (84); HRMS calculated for $C_{24}H_{23}ClN_4O_2$: 434.1504, found 434.1490. Anal. calcd for $C_{24}H_{23}ClN_4O \cdot 0.5\ H_2O$: C, 64.93; H, 5.45; N, 12.62. Found: C, 64.74; H, 5.46; N, 12.38.

H. 7-(3-(1,1-Dimethylethyl)-1,2,4-oxadiaz-5-yl)-1-(4-methylpiperazin-1-yl)naphthalene Sodium (0.112 g, 4.9 mmol), hydroxylamine hydrochloride (0.35 g, 5 mmol), and trimethylacetonitrile (0.334 g, 2.0 mmol) and methanol (5 mL) were used to prepare trimethylacetamidoxime (0.35 g, 100%) as described above.

Trimethylacetamidoxime (0.35 g, assumed 2.0 mmol), sodium hydride (60% dispersion in oil, 0.090 g, 2.2 mmol), benzyl 1-(4-methylpiperazin-1-yl)naphthalene-7-carboxylate (0.360 g, 1.0 mmol), and anhydrous tetrahydrofuran (15 mL total) were used to form the title compound as described above. Chromatographic purification using elution with ethyl acetate/methanol/triethylamine [40:1:1] afforded the title compound (0.168 g, 0.48 mmol, 48%) as a pale yellow foam: $^1$H NMR (CDCl$_3$) δ 9.00 (br s, 1H), 8.16 (dd, J=1.6 and 8.6 Hz, 1H), 7.94 (d, J=8.6 Hz, 1H), 7.59–7.49 (m, 2H), 7.18 (dd, J=1.1 and 7.2 Hz, 1H), 3.23 (br m, 4H), 2.84 (br m, 4H), 2.51 (s, 3H), 1.49 (s, 9H); LRMS (m/z, relative intensity) 351 (18), 350 (M$^+$, 100), 335 (10), 293 (29), 182 (29), 71 (50), 70 (46); HRMS calculated for $C_{21}H_{26}N_4O$ 350.2101, found 350.2111. Anal. calculated for $C_{21}H_{26}N_4O \cdot H_2O$: C, 68.45; H, 7.66; N, 15.20. Found: 68.14; H, 7.32; N, 14.91.

I. 7-(3-(3-Chlorophenylmethyl)-1,2,4-oxadiaz-5-yl)-1-(4-methylpiperazin-1-yl)naphthalene Sodium (0.120 g, 5.2 mol), hydroxylamine hydrochloride (0.35 g, 5.0 mmol), and (3-chlorophenyl)acetonitrile (0.303 g, 2.0 mmol) and methanol (5 mL) were used to prepare (3-chlorophenyl)acetamidoxime (0.42 g, >100%) as described above.

(3-Chlorophenyl)acetamidoxime (0.42 g, assumed 2.0 mmol), sodium hydride (60% dispersion in oil, 0.093 g, 2.3 mmol), benzyl 1-(4-methylpiperazin-1-yl)naphthalene-7-carboxylate (0.360 g, 1.00 mmol), and anhydrous tetrahydrofuran (12 mL total) were to used form the title compound as described above. Chromatographic purification using elution with 10% methanol in ethyl acetate afforded the title compound (0.105 g, 0.25 mmol, 25%) as a pale yellow powder: $^{13}$C NMR (CDCl$_3$) δ 176.4, 169.6, 150.9, 137.5, 136.6, 134.5, 129.9, 129.5, 129.3, 128.7, 128.3, 127.4, 127.3, 125.2, 123.9, 123.2, 120.7, 116.0, 55.5, 53.2, 46.1, 32.1; LRMS (m/z, relative intensity) 420 ([M$^+$ with $^{37}$Cl], 29), 419 (32), 418 (M$^+$ with $^{35}$Cl], 100), 403 (14), 350 (53), 293 (28), 182 (39), 154 (39), 71 (95), 70 (63); HRMS calculated for $C_{24}H_{23}ClN_4O$: 418.1555, found 418.1583. Anal. calculated for $C_{24}H_{23}ClN_4O \cdot 0.5\ H_2O$: C, 67.36; H, 5.65; N, 13.09. Found: C, 67.28; H, 5.54; N, 12.95.

J. 7-(3-Phenylpropyl-1,2,4-oxadiaz-5-yl)-1-(4-methylpiperazin-1-yl)naphthalene

Sodium (0.235 g, 10.2 mol), hydroxylamine hydrochloride (0.70 g, 10.1 mmol), and 4-phenylbutyronitrile (0.58 g, 4.0 mmol) and methanol (6 mL) were used to prepare 4-phenylbutyroamidoxime (0.79 g, >100%) as described above.

4-Phenylbutyroacetamidoxime (0.79 g, assumed 4.0 mmol), sodium hydride (60% dispersion in oil, 0.210 g, 5.2 mmol), benzyl 1-(4-methylpiperazin-1-yl)naphthalene-7-carboxylate (0.720 g, 2.00 mmol), and anhydrous tetrahydrofuran (20 mL total) were to used form the title compound as described above. Chromatographic purification using elution with 4–10% methanol gradient in ethyl acetate afforded the title compound (0.363 g, 0.88 mmol, 44%) as a pale yellow amorphous solid: $^1$H NMR (acetone-d$_6$) δ 9.01 (br s, 1H), 8.11 (dd, J=8.6 and 1.7 Hz, 1H), 8.04 (d, J=8.5 Hz, 1H ), 7.66 (d, J=8.2 Hz, 1H), 7.56 (t, J=8.2 Hz, 1H), 7.32–7.15 (m, 6H), 3.12 (br m, 4H), 2.83 (t, J=7.4 Hz, 2H), 2.77 (t, J=7.4 Hz, 2H), 2.70 (br m, 4H), 2.35 (s, 3H), 2.18–2.08 (m, 2H); $^{13}$C NMR (CDCl$_3$) δ 176.3, 171.9, 151.8, 142.4, 137.4, 130.4, 129.6, 129.3, 129.1, 129.0, 126.6, 125.4, 124.4, 123.9, 121.6, 116.8, 56.1, 53.9, 46.2, 35.5, 25.9; FAB LRMS (m/z, relative intensity) 413 (MH$^+$, 100).

EXAMPLE 53

General Procedure for the Aminolysis of 1-(4-Methylpiperazin-1-yl)naphthalene-7-carboxylic acid To a stirred solution of 1-(4-methylpiperazin-1-yl)naphthalene-7-carboxylic acid (0.270 g, 1.00 mmol) in anhydrous tetrahydrofuran (5 mL) at room temperature was added carbonyl diimidazole (0.178 mg, 1.10 mmol, 1.1 eq) directly as a solid. The resulting reaction solution was stirred at room temperature under nitrogen for 3 hours. The appropriate amine (1.1 mmol, 1.1 eq) was then added, and the resulting reaction solution was stirred at room temperature under nitrogen for 16 hours. A saturated solution of sodium hydrogen carbonate was added, and the resulting aqueous mixture was extracted with ethyl acetate (2×25 mL). The organic extracts were combined, dried (MgSO$_4$), and evaporated under reduced pressure. Column chromatography of the residue using silica gel (approximately 50 g) and an appropriate solvent system afforded the corresponding 1-(4-methylpiperazin-1-yl)naphthalene-7-carboxamide.

Using this procedure, the following compounds were prepared:

A. N-(2-(Indol-3-yl)ethyl)-1-(4-methylpiperazin-1-yl)naphthalene-7-carboxamide

Tryptamine was the amine used. Chromatography using elution with 20% methanol in ethyl acetate afforded the title compound (63%) as a white foam: R$_f$=0.20 [20% methanol in ethyl acetate]; $^{13}$C NMR (acetone-d$_6$) δ 167.9, 151.7, 137.7, 136.8, 132.7, 129.2, 128.9, 128.6, 128.3, 124.6, 124.3, 123.6, 123.3, 122.0, 119.3, 119.3, 116.0, 113.4, 112.1, 56.0, 53.8, 46.3, 41.5, 26.3; LRMS (m/z, relative intensity) 412 (M$^+$, 100), 269 (41), 143 (60), 130 (36), 71 (43), 70 (30); HRMS calculated for $C_{26}H_{28}N_4O$ 412.2229, found 412.2305.

B. 1-(4-Methylpiperazin-1-yl)naphthalene-7-carboxamide

Ammonia was the amine used. Extraction of the reaction led directly to the title compound (35%) as a white foam: $^1$H NMR (CDCl$_3$) δ 8.71 (br s, 1H), 7.89 (d, J=8.5 Hz, 1H), 7.85 (dd, J=1.6 and 8.5 Hz, 1H), 7.59 (br d, J=8.1 Hz, 1H), 7.51 (t, J=7.3 Hz, 1H), 7.17 (d, J=1.1 and 7.2 Hz, 1H), 6.4–5.8 (br, 2H), 3.17 (br m, 4H), 2.76 (br m, 4H), 2.45 (s, 3H) ; $^{13}$C NMR (CDCl$_3$) δ 170.0, 150.8, 136.4, 130.1, 129.0, 128.2, 128.0, 123.8, 123.2, 115.7, 55.5, 53.2, 46.1; HRMS calculated for C$_{16}$H$_{19}$N$_3$O 269.1530, found 269.1542.

C. N-(4-Pyridylmethyl)-1-(4-methylpiperazin-1-yl) naphthalene-7-carboxamide 4-(Aminomethyl)pyridine was the amine used. Chromatography using elution with methylene chloride/methanol/ ammonium hydroxide [10:4:0.4] afforded the title compound as an imidazoyl salt. This material was dissolved in methylene chloride (25 mL), and this solution was extracted with a solution of sodium carbonate (1M, 2×20 mL). The ethyl acetate layer was dried (K$_2$CO$_3$) and evaporated under reduced pressure to afford the title compound (35%) as a pale yellow foam: LRMS (m/z, relative intensity) 360 (M$^+$, 50), 345 (46), 317 (100), 290 (27), 225 (27), 154 (35), 71 (66), 70 (48); HRMS calculated for C$_{22}$H$_{24}$N$_4$O 360.1945, found 360.1932. Anal. calcd for C$_{22}$H$_{24}$N$_4$O H$_2$O: C, 69.82; H, 6.92; N, 14.80. Found: C, 69.82; H, 6.91; N, 14.53.

D. N-(3-Pyridylmethyl)-1-(4-methylpiperazin-1-yl) naphthalene-7-carboxamide 3-(Aminomethyl)pyridine was the amine used. Chromatography using elution with methylene chloride/methanol/ ammonium hydroxide [20:1:0.1] afforded the title compound as an imidazoyl salt. This material was dissolved in methylene chloride (25 mL), and this solution was extracted with a solution of sodium carbonate (1M, 2×20 mL). The ethyl acetate layer was dried (K$_2$CO$_3$) and evaporated under reduced pressure to afford the title compound (17%) as a white amorphous solid: $^{13}$C NMR (CD$_3$OD) δ 170.7, 160.7, 151.9, 149.2, 148.6, 137.6, 137.2, 137.0, 132.0, 130.0, 129.5, 129.2, 125.2, 125.2, 124.4, 116.9, 56.4, 53.8, 46.2, 42.2; LRMS (m/z, relative intensity) 360 (M$^+$, 36), 345 (43), 317 (100), 290 (30), 242 (30), 208 (35), 71 (75); HRMS calculated for C$_{22}$H$_{24}$N$_4$O 360.1945, found 360.1946.

E. N-(2-Pyridylmethyl)1-(4-methylpiperazin-1-yl) naphthalene-7-carboxamide 2-(Aminomethyl)pyridine was the amine used. Chromatography using elution with methylene chloride/methanol/ ammonium hydroxide [9:1:0.1] afforded the title compound as an imidazoyl salt. This material was dissolved in methylene chloride (25 mL), and this solution was extracted with a solution of sodium carbonate (1M, 2×20 mL). The ethyl acetate layer was dried (K$_2$CO$_3$) and evaporated under reduced pressure to afford the title compound (19%) as a pale yellow oil: $^{13}$C NMR (CD$_3$OD) δ 170.7, 159.5, 151.9, 149.8, 149.6, 138.9, 137.8, 132.1, 130.0, 129.5, 129.1, 125.2, 124.4, 124.0, 122.7, 116.9, 56.4, 53.8, 46.2, 46.0; LRMS (m/z, relative intensity) 360 (M$^+$, 100), 345 (71), 317 (38), 290 (48), 182 (64), 71 (89); HRMS calculated for C$_{22}$H$_{24}$N$_4$O 360.1945, found 360.1932.

F. N-(4-Pyridylethyl)-1-(4-methylpiperazin-1-yl) naphthalene-7-carboxamide 2-(2-Aminoethyl)pyridine was the amine used. Chromatography using elution with 20% methanol in ethyl acetate afforded the title compound as an imidazoyl salt. This material was dissolved in methylene chloride (25 mL), and this solution was extracted with a solution of sodium carbonate (1M, 2×20 mL). The ethyl acetate layer was dried (K$_2$CO$_3$) and evaporated under reduced pressure to afford the title compound (54%) as a clear, pale brown oil: R$_f$=0.15 in 20% methanol in ethyl acetate; LRMS (m/z, relative intensity) 374 (M$^+$, 50), 359 (100), 331 (34), 304 (63), 208 (43), 182 (73), 149 (83); HRMS calculated for C$_{26}$H$_{26}$N$_4$O 374.2106, found 374.2111.

EXAMPLE 54

N-(5-(1,1,-Dimethylethyl)-1,2,4-oxadiaz-3-ylmethyl)-1-(4-methylpiperazin-1-yl)naphthalene-7-carboxamide To solution of 1-(4-methylpiperazin-1-yl)naphthalene-7-carboxamide (0.100 g, 0.37 mmol) in anhydrous tetrahydrofuran (5 mL) at –10° C. was added lithium diisopropylamide (1.5M in tetrahydrofuran, 0.30 mL, 0.45 mmol, 1.2 equivalents), and the resulting reaction solution was allowed to warm to room temperature. Then, 3-(chloromethyl)-5-(11-dimethylethyl)-1,2,4-oxadiazole(0.078 g, 0.45 mmol, 1.2 eq) was added, and the resulting reaction solution was heated at reflux under nitrogen for 22 hours. A saturated solution of sodium hydrogen carbonate was then added, and the resulting aqueous mixture was extracted with ethyl acetate (2×20 mL) . The organic extracts were combined, dried (MgSO$_4$), and evaporated under reduced pressure. Column chromatography of the residue using silica gel (approximately 25 g) and elution with 5% triethylamine in ethyl acetate afforded the title compound (0.035 g, 0.09 mmol, 23%) as a yellow oil: R$_f$=0.40 in ethyl acetate/ methanol/triethylamine [8:1:1]; $^1$H NMR (CDCl$_3$) δ 8.88 (br s, 1H), 7.84 (s, 2H), 7.54 (d, J=8.0 Hz, 1H), 7.46 (br t, J=8.2 Hz, 1H), 7.12 (dd, J=1.0 and 7.3 Hz), 6.98 (br t, NH), 4.83 (d, J=5.4 Hz, 2H), 3.13 (br m, 4H), 2.73 (br m, 4H), 2.40 (s, 3H), 1.43 (s, 9H); LRMS (m/z, relative intensity) 407 (M$^+$, 46), 392 (20), 182 (45), 151 (57), 113 (54), 71 (100), 70 (34); HRMS calculated for C$_{23}$H$_{29}$N$_5$O$_2$ 407.2315, found 407.2310.

Preparation 1

8-(4-methylpiperazin-1-yl)naphthalen-2-ol

To a stirring solution of 8-amino-2-naphthol (3.28 g, 20 mmol, Aldrich Chem. Co.) in 100 mL of acetonitrile was added sodium bicarbonate (7.42 g, 88 mmol), sodium iodide (6.72 g, 44 mmol) and mechlorethamine hydrochloride (4.32 g, 22 mmol). Under nitrogen, the reaction was heated to reflux and stirred for another 2 hr. The reaction mixture was then allowed to cool to room temperature and was stirred overnight. A thin layer chromatography (tlc) using methylene chloride: methanol: conc. ammonium hydroxide (90:10:1) showed the more polar product (R$_f$ 0.25) with only a trace of the starting naphthol. Silica gel (4.5 g) was added and the reaction mixture was concentrated in vacuo to a dry purple solid. This was added to a column of silica gel (ca. 400 g) and eluted with 2 L volumes of CH$_2$Cl$_2$, CH$_2$Cl$_2$:CH$_3$OH (40:1), CH$_2$Cl$_2$:CH$_3$OH:conc. NH$_4$OH (20:1:0.1) and finally 4 L of CH$_2$Cl$_2$:CH$_3$OH:conc. NH$_4$CH (10:1:0.1). The appropriate fractions were combined to yield a purple-black solid, 5.26 g, mp 184°–185° C.

$^1$H NMR (CD$_3$OD) δ 2.40 (s, 3H), 2.72 (bs, 4H), 3.05 (bs, 4H), 7.05 (d, 2H), 7.18 (t, 1H), 7.45(m, 2H), 7.67 (d, 1H).

Mass spectrum: m/e 242 (M$^+$)

Preparation 2

Trifluoromethanesulfonic acid 8-(4-methylpiperazin-1-yl)naphthalen-2-yl ester

To a stirred suspension of 8-(4-methylpiperazin-1-yl) naphthalen-2-ol (5.0 g, 20 mmol) in anhydrous methylene chloride (50 mL), cooled to –78° C. was added triethylamine (20 mL) followed by trifluoromethanesulfonic anhydride (3.9 mL). After a further hr at –78° C., the cooling bath was removed, silica gel (4.5 g) was added and the solvent was removed in vacuo. The resulting slurry was added to a column of 400 g of silica gel and the product was eluted with an ethyl acetate:methanol gradient (100:0 to 80:20) . The product fractions were concentrated in vacuo to provide the title product, 4.32 g.

Preparation 3

8-(4-Methylpiperazin-1-yl)naphthalene-2-carboxylic acid benzyl ester

A mixture of the preceding compound (34 g, 90.8 mmol, 1.0 equiv.), benzyl alcohol (170 mL), bis (triphenylphosphine)palladium(II) chloride (6.2 g, 8.8 mmol, 0.1 equiv.), lithium chloride (0.44 g, 10.5 mmol, 0.1 equiv.) and triethylamine (32 mL) was shaken under an atmosphere of carbon monoxide (50 psi) at 70° C. for 6.5 hours. The resulting reaction solution was directly filtered through silica gel (2 kg, pre-wet with ethyl acetate) and eluted with ethyl acetate (8 L) followed by 5% methanol in ethyl acetate to afford the title compound (28.04 g, 77.8 mmol, 86%) as a pale brown foam. $^1$H NMR (acetone-$D_6$) δ 9.00 (d, J=0.7 Hz, 1H), 8.04 (dd, J=8.6 and 1.7 Hz, 1H), 7.96 (d, J=8.6 Hz, 1H), 7.66 (d, J=8.2 Hz, 1H), 7.59–7.53 (m, 3H), 7.47–7.36 (m, 3H), 7.22 (dd, J=7.3 and 1.1 Hz, 1H), 5.43 (s, 2H), 3.20 (br m, 4H), 2.91 (br m, 4H), 2.54 (s, 3H). LRMS (m/e, relative intensity) 361 (M+, 29). HRMS calculated for $C_{23}H_{24}N_2O_2$: 360.1839. Found: 360.1832.

Preparation 4

8-(4-Methylpiperazin-1-yl)naphthalene-2-carboxylic acid

A mixture of 8-(4-methylpiperazin-1-yl)naphthalene-2-carboxylic acid benzyl ester (0.20 g, 5.55 mmol) and Pd(OH) on carbon (0.11 g) in 2 mL of ethanol was hydrogenated on a Parr shaker apparatus at 50 psi for 5 hr. After diluting with ethanol and filtering through diatomaceous earth, the solvent was removed in vacuo to yield the title product as a foam, 138 mg.

Preparation 5

1-(1-Methylpiperidin-4-yl)-7-trifluoromethanesulfonyloxynaphthalene

In two side by side reactions, 8-bromo-2-tetralone (7.0 g, 31.25 mmol) and N-bromosuccinimide (5.84 g, 32.8 mmol) were combined in carbon tetrachloride and refluxed 45 min. The reactions were cooled, filtered through diatomaceous earth (Celite™), and combined for workup. The organic solution was washed with saturated aqueous sodium bicarbonate and brine followed by drying through phase separating filter paper (1PS) and concentrated to give 14.44 g (104% crude) of 8-bromo-2-naphthol as a brown solid which was suitable for further reaction. A sample dissolved in methylene chloride and treated with activated carbon, concentrated, and triturated with hexane had: mp 96°–100° C.; $^1$HNMR (250 MHz, $CDCl_3$) δ 7.79–7.73 (m, 3H), 7.56 (d, J=4.5 Hz, 1H), 7.22–7.14 (m, 3H). HRMS m/e calculated for $C_{10}H_7BrO$: 221.9680. Observed m/e: 221.9664.

In two side by side reactions, 8-bromo-2-naphthol (7.22 g, 32.5 mmol) was dissolved in tetrahydrofuran (200 mL) and chilled to −78° C. Butyl lithium (31.2 mL, 74.8 mmol) was rapidly added (1–2 min) and the solution was stirred for 12 min. 1-Methyl-4-piperidone (4.22 mL, 34.2 mmol, dissolved in 10 mL of tetrahydrofuran) was added dropwise to the solution with a 10 mL,tetrahydrofuran rinse. The reaction was stirred at −78° C. for an additional 30 min, then allowed to warm to room temperature. The reactions were combined and concentrated directly onto silica gel and flash chromatographed (3.5x4 inches of silica gel, packed with ethyl acetate). Elution proceeded as follows: ethyl acetate, 500 mL, nil; 2% methanol/1% triethylamine/ethyl acetate, 1000 mL, nil; 4% methanol/2% triethylamine/ethyl acetate, 2000 mL, nil; 6% methanol/3% triethylamine/ethyl acetate, 3000 mL, 7.64 g of pure 1-(1-methyl-4-hydroxypiperidin-4-yl)-7-hydroxynaphthalene. Continued elution with 8% methanol/4% triethylamine/ethyl acetate, 2000 mL, 4.32 g of additional product which was significantly contaminated with a triethylamine derived impurity, possibly a salt. A sample of the pure product recrystallized from dioxane as a ⅓ methanolate had: mp 206°–208° C. (dec.); $^1$HNMR (250 MHz, $DMSO_{d6}$) δ 9.63 (s, 1H), 8.20 (d, J=2 Hz, 1H), 7.73 (d, J=9 Hz, 1H), 7.65 (d, J=8 Hz, 1H), 7.47 (d, J=6.5 Hz, 1H), 7.18 (t, J=7.5 Hz, 1H), 7.02 (dd, J=2.5, 9 Hz, 1H), 4.96 (s, 1H) 2.70–2.46 (m, 4H partially obscured by the NMR solvent), 2.22 (s, 3H), 2.21–2.00 (m, 4H) . There were also two singlets at δ 5.76 and 3.56 which integrated for the ⅓ methanolate. Analysis calculated for $C_{16}H_{19}N_2O·0.33$ $CH_4O$: C, 73.29; H, 7.53; N, 5.23. Found: C, 73.61; H, 7.62; N, 5.32.

A mixture of 1-(1-methyl-4-hydroxypiperidin-4-yl)-7-hydroxynaphthalene (7.64 g, 29.7 mmol) and p-toluenesulfonic acid (6.78 g, 35.7 mmol) in dioxane (250 mL) was refluxed overnight. The solvent was removed at reduced pressure and the residue was taken up in methylene chloride. The naphthol product was extracted from this organic phase with 1N sodium hydroxide, 4N sodium hydroxide and then 1N sodium hydroxide. The combined basic aqueous phase was neutralized to pH 8 with saturated aqueous sodium bicarbonate and extracted with warm chloroform (3×, two phase mixture vigorously magnetically stirred while heat was applied by means of a hot plate.) The combined organic phase (still warm) was washed with brine, dried over calcium sulfate and concentrated to afford 5.01 g (83% for this step) of 1-(1-methyl-1,2,3,6-tetrahydropyrid-4-yl)-7-hydroxynaphthalene as a tan solid. A sample recrystallized from ethyl acetate had: mp 182.5°–184° C.; $^1$H NMR (250 MHz, $CDCl_3$) δ 9.15 (s, 1H), 7.98 (d, J=2.5 Hz, 1H), 7.69 (d, J=9 Hz, 1H), 7.65 (d, J=8 Hz, 1H), 7.25–7.12 (m, 2H), 7.03 (dd, J=2.5, 9 Hz, 1H), 5.70 (sym m, 1H), 3.32 (sym m, 2H), 2.92 (t, J=6 Hz, 2H), 2.70–2.60 (m, 2H), 2.66 (s, 3H). Analysis calculated for $C_{16}H_{17}NO·0.25$ $H_2O$: C, 78.82; H, 7.23; N, 5.74. Found: C, 78.81; H, 7.21; N, 5.83.

The 4.32 g of impure 1-(1-methyl-4-hydroxypiperidin-4-yl)-7-hydroxynaphthalene was subjected to the identical dehydration conditions above and 1.13 g of crude product was obtained. Recrystallization from ethyl acetate gave 0.855 g of 1-(1-methyl-1,2,3,6-tetrahydropyrid-4-yl)-7-hydroxynaphthalene as white crystals. Thus a total of 5.865 g was obtained for a total yield of 39% for the above two steps.

A mixture of 1-(1-methyl-1,2,3,6-tetrahydropyrid-4-yl)-7-hydroxynaphthalene (5.865 g, 24.54 mmol), 20% palladium on carbon (5.9 g), methanol (210 mL), and acetic acid (30 mL) was hydrogenated for 6.5 h (initial pressure—40 psi) . The mixture was filtered through celite and the pad was rinsed well with methanol. The solvent was removed at reduced pressure and the residue was neutralized with saturated aqueous sodium bicarbonate. This mixture was extracted with hot chloroform (3×) and with warm methylene chloride (1×). The combined organic phase (still hot) was washed with brine (prewarmed to the same temperature as the chloroform solution, approximately 60° C.), dried over calcium sulfate and concentrated to afford 2.0 g of brown solid product. The aqueous bicarbonate phase above was concentrated to dryness. The residue was extracted with hot chloroform and filtered. The hot extraction process was repeated successively with methylene chloride, ethanol and once again with chloroform. The combined solutions were concentrated to afford an additional 3.26 g of brown solid. In this fashion, 5.26 g (89%) of 1-(1-methylpiperidin-4-yl)-7-hydroxynaphthalene was obtained. The material was suitable for use in the next step without purification. A sample recrystallized from methanol had: mp 196.5°–199° C.; $^1$H NMR (250 MHz, $CDCl_3$) δ 7.76 (d, J=9 Hz, 1H), 7.62 (d, J=8 Hz, 1H), 7.40 (d, J=2 Hz, 1H), 7.26 (sym m, partially obscured by the NMR solvent, 2H), 7.09 (dd, J=2.5, 9 Hz, 1H), 3.26–3.08 (m, 3H), 2.42 (s, 3H), 2.35–2.20 (m, 2H), 2.16–1.92 (m, 4H). Analysis calculated for $C_{16}H_{19}NO$: C, 79.63; H, 7.94; N, 5.80. Found: C, 79.22; H, 8.18; N, 5.83.

A solution of 1-(1-methylpiperidin-4-yl)-7-hydroxynaphthalene (3.47 g, 14.4 mmol) in methylene chloride (150 mL) was treated with triethylamine (9.03 mL, 64.8 mmol) and chilled to −78° C. Triflic anhydride (3.03 mL, 18.0 mmol) was added dropwise to the reaction with a 10 mL methylene chloride rinse. The reaction was allowed to warm to room temperature and stir overnight. The reaction was concentrated with a nitrogen stream and the residue was partitioned between methylene chloride and saturated aqueous sodium bicarbonate. The phases were separated and the organic phase was washed with brine, dried over calcium sulfate and concentrated. The residue was flash chromatographed on silica gel (2×3 inches packed in 75% ethyl acetate/hexane). Elution proceeded as follows: 75% ethyl acetate/hexane, 500 mL, nil; ethyl acetate, 600 mL, nil; 2% methanol/1% triethylamine/ethyl acetate, 600 mL, nil; 5% methanol/2% triethylamine/ethyl acetate, 600 mL, 2.74 g (51%) of 1-(1-methylpiperidin-4-yl)-7-trifluoromethanesulfonyloxynaphthalene as a light brown crystalline solid suitable for further reaction. A sample recrystallized from ethyl acetate/hexane had: mp 144°–146° C.; $^1$H NMR (250 MHz, $CDCl_3$) δ 7.96–7.91 (m, 2H), 7.76 (dd, J=2.5, 7 Hz, 1H), 7.58–7.51 (m, 2H), 7.36 (dd, J=2.5, 9 Hz, 1H), 3.25–3.12 (m, 3H), 2.48 (s, 3H), 2.37 (sym m, 2H), 2.19–1.95 (m, 4H). HRMS m/e calculated for $C_{17}H_{18}F_3NO_3S$: 373.0954. Observed m/e: 373.0898.

Synthesis of intermediates used in the above examples are described in the preparations below.

Preparation 6

7-hydroxy-1-(4-methyl-1-piperazinyl)-3,4-dihydronaphthalene

7-Hydroxy-α-tetralone (1.0 g, 6.17 mmol, Corey and Estreicher, Tetrahedron Lett., 1981, 22, 603) and 1-methylpiperazine (2.2 mL, 19.83 mmol) were dissolved in dry THF (90 mL) and chilled to 0° C. Titanium tetrachloride (0.91 mL, 8.3 mmol) was allowed to run down the side of the reaction vessel into the reaction via syringe to give a vigorous reaction which caused the solution to turn orange-red. The mixture was allowed to warm to ambient temperature and stir 1.5 hours. A 2:1 mixture of water and concentrated ammonium hydroxide (90 mL) was added and the mixture was extracted with ethyl acetate. The organic phase was dried over calcium sulfate and concentrated to give 1.48 g of crude enamine which was used immediately without characterization. (This enamine was not stable to chromatography but did show a characteristic signal in the $^1$H NMR for the enamine vinyl proton at 5.28 ppm with a 4.7 Hz coupling constant).

Preparation 7

7-Hydroxy-1-(4-methyl-1-piperazinyl)-naphthalene

10% Palladium on carbon (1.16 g) and 7-hydroxy-1-(4-methyl-1-piperazinyl)-2,3-dihydronaphthalene (1.48 g, 6.06 mmol) were slurried in toluene (100 mL) and refluxed 16.5 h. The mixture was cooled, filtered, and concentrated. The product was purified by flash chromatography on silica gel (1×6 inches). Elution with 50 % ethyl acetate/hexane followed by 100% ethyl acetate gave 0.51 g (34%) of the title product as a light pink foam. A sample was recrystallized from ether to give a cream colored solid for analysis: mp 184°–185° C. Analysis calculated for $C_{15}H_{18}N_2O$: C, 74.35; H, 7.49; N, 11.56. Found: C, 74.05;H, 7.03; N, 11.42.

Preparation 8

7-Trimethylstannyl-1-(4-methyl-1-piperazinyl)-naphthalene 7-trifluoromethylsulfonyloxy-1-(4-methyl-1-piperazinyl)-naphthalene (2.0 g, 5.34 mmol), hexamethylditin (1.92 g, 5.86 mmol), lithium chloride (0.68 g, 16 mmol), tetrakis (triphenylphosphine) palladium (0.24 g, 0.21 mmol) and butylated hydroxytoluene (a few crystals, antioxidant) were combined in dry dioxane (50 mL) and refluxed 45 minutes. The mixture was cooled and quenched with saturated ammonium chloride (50 mL). The mixture was extracted with ether (2×) and the combined organic phase was washed with brine, dried over magnesium sulfate, and concentrated to a brown oil. Flash chromatography on silica gel (2×4 inches) with 50% ethyl acetate/hexane elution gave 0.77 g (37%) of the title product as a light brown oil which slowly solidified. The product was suitable for use in subsequent reactions but was not analytically pure: $^1$H NMR δ 8.36 (s with Sn coupling, 1H ), 7.80 (d, J=8 Hz, 1H), 7.61–7.51 (m, 2H), 7.40 (t, J=8 Hz, 1H), 7.09 (dd, J=1, 7.5 Hz, 1H), 3.2 (br s, 4H), 2.75 (br s, 4H), 2.46 (s, 3H), 0.39 (s with Sn coupling of 55.0 and 52.5 Hz, 9H).

Preparation 9

5-Chloromethyl-3-phenyl-1,2 4-oxadiazole

A solution of benzamidoxime (0.77 g, 5.68 mmol) and triethylamine (0.95 mL, 0.82 mmol) in toluene (10 mL) was treated with 0.45 mL (5.65 mmol) of chloroacetyl chloride at room temperature for 30 min., refluxed for 18 hours, cooled to room temperature and concentrated in vacuo. The residue was diluted with water, and extracted with ethyl acetate. The organic extracts were then washed with water and dried with $MgSO_4$. Concentration in vacuo gave an oil which was chromatographed on silica gel using ethyl acetate, hexanes (1.9), giving 0.24 of the title compound as a light yellow oil which solidified on standing. $^1$H NMR (250 MHz, $CDC_3$) δ 8.1 (m, 2H), 7.5 (m, 3H), 4.8 (s, 2H).

In the same manner, the following analogs were prepared:

5-Chloromethyl-3-(2-methoxyphenyl-1,2,4-oxadiazole white semi-solid, $^1$H NMR (250 MHz, $CDCl_3$) δ 8.0 (dd, 2H), 7.5 (m, 1H), 7.0 (m, 2H), 4.8 (s, 2H), 4.0 (s, 3H).

5-Chloromethyl-3-(4-methoxyphenyl)-1,2,4-oxadiazole, semi-solid, $^1$H NMR (250 MHz, $CDCl_3$) δ 8.0 (d, 2H), 7.0 (d, 2H), 4.8 (s, 2H), 4.0 (s, 3H); mass spectrum m/e 224 ($M^+$).

5-Chloromethyl-3-(4-chlorophenyl)-1,2,4-oxadiazole, semi-solid, $^1$H NMR (250 MHz, $CDCl_3$) δ 8.0 (d, 2H), 7.5 (d, 2H), 4.8 (s, 2H); mass spectrum: m/e 228 ($M^+$).

Preparation 10

3-Chloromethyl-5-(4-chlorophenyl)-1,2,4-oxadiazole

A solution of 2-chloroacetamidoxime (0.5 g) and sodium bicarbonate (0.78 g) in 10 mL of anhydrous acetone was treated with 4-chlorobenzoyl chloride (0.58 mL) at room temperature for 2 hours, concentrated in vacuo, dissolved in water and extracted with ethyl acetate. The organic layers were combined, dried with $MgSO_4$ and concentrated to a semi-solid. This material was redissolved in toluene (50 mL). refluxed under nitrogen for 15 hours, cooled and absorbed on to silica gel. Chromatography using ethyl acetate:hexane (1:9) gave the pure title product as a light yellow solid, mp 79°–80° C. Mass spectrum m/e: 228 (M+), $^1$H NMR (250 MHz, CDCl$_3$) δ 8.1 (d, 2H), 7.5 (d, 2H), 4.7 (s, 2H).

Preparation 11

5-Bromo-8-(4-methylpiperazin-1-yl)naphthalene-2-carboxylic acid 4-chloro-benzylamide To a solution of 8-(4-methylpiperazin-1-yl)naphthalene-2-carboxylic acid 4-chlorobenzylamide (0.100 g, 0.256 mmol) and sodium bicarbonate (0.106 g, 1.26 mmol) in 2 mL of methanol was added bromine (26 μL, 0.50 mmol) in 0.5 mL of dichloromethane. After stirring for 30 min at room temperature the reaction mixture was evaporated in vacuo and the residue was treated with water and extracted with dichloromethane. The organic extracts were dried with MgSO$_4$ and concentrated to a yellow oil. Chromatography on silica gel using methanol/conc. ammonium hydroxide/dichloromethane (2.0/0.2/97.9) gave 0.040 g (33%) of the title product as an oil which slowly solidified, mp 103° C. (dec). Mass spectrum: m/e 475 (M+1), 395 (M±Br), $^1$H NMR (CDCl$_3$) δ 8.6 (d, 1H), 8.3 (d, 1H), 7.8 (dd, 1H), 7.7 (d, 1H). 7.3 (s, 4H), 7.0 (d, 1H), 6.8 (t, 1H), 4.7 (d, 2H), 3.1 (bs, 4H), 2.7 (bs, 4H), 2.5 (s, 3H).

In the same manner, 8-(4-methylpiperazin-1-yl)naphthalene-2-carboxylic acid 4-chloro-3-iodo-benzylamide was converted in 72% yield to 5-bromo-8-(4-methylpiperazin-1-yl)-naphthalene-2-carboxylic acid 4-chloro-3-iodobenzylamide, mp 131° C. (dec). Mass spectrum: m/e 808,598. $^1$H NMR (CDCl$_3$) δ 8.7 (d, 1H), 8.2 (d, 1H), 7.5 (m, 2H), 7.7 (d, 1H), 7.4 (d, 1H), 7.3 (dd, 1H), 7.0 (d, 1H), 6.7 (t, 1H), 4.7 (d, 2H), 3.2 (bs, 4H), 2.7 (bs, 4H), 2.5 (s, 3H).

I claim:

1. A method of inhibiting cell growth in human small cell lung carcinoma comprising administering to a mammal in need of said treatment a cell growth inhibitory effective amount of a compound of the formula

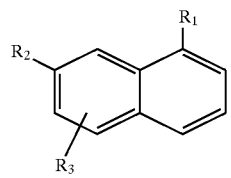

where R$_1$ is of the formulae

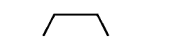

or

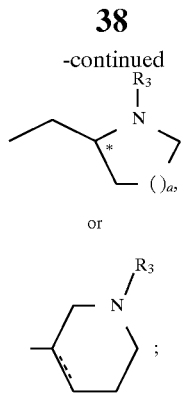

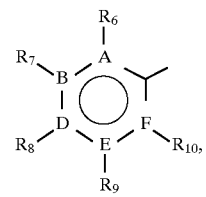

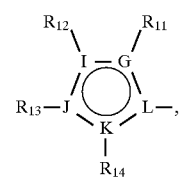

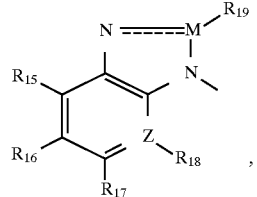

R$_2$ is —R$_4$, —O—R$_4$, —O—S(O)$_2$—R$_4$, —NR$_4$R$_6$, R$_4$—(CH$_2$)$_b$—NH(C=X)—(CH$_2$)$_c$—, R$_4$—(CH$_2$)$_b$—O(C=O)NH—(CH$_2$)$_c$—(CH=))NH—, R$_4$—(C=O)NH—(C=O)NH—, —(CH$_2$)$_b$—NH(C=X)—(CH$_2$)$_c$—R$_4$, R$_4$—(CH$_2$)$_b$—O(C=O)—(CH$_2$)$_c$—, —(CH$_2$)$_b$—O(C=O )—(CH$_2$)$_c$—R$_4$, —NH(C=X)NH—R$_4$, R$_4$—O(C=O)O—, —O(C=O)NH—R$_4$, R$_4$—O(C=O)NH—, —(CH$_2$)$_b$—(C=O)—(CH$_2$)$_c$—R$_4$, —NH—S(O)$_2$—R$_4$, —C(OH)R$_4$R$_5$, —CH(OH)—R$_4$, —(C=O)—NR$_4$R$_5$, —CN, —NO$_2$, substituted C$_1$ to C$_6$ alkyl, substituted or unsubstituted C$_1$ to C$_6$ alkenyl, or substituted or unsubstituted C$_1$ to C$_6$ alkynyl, said substituted moieties substituted with a moiety of the formulae —R$_4$, —R$_4$R$_5$, —O—R$_4$, or —S(O)$_d$—R$_4$;

R$_3$ is hydrogen, CH$_3$OCH$_2$CH$_2$, C$_1$ to C$_6$ alkyl, C$_1$ to C$_6$ alkylaryl, or aryl;

R$_4$ and R$_5$ are each independently hydrogen, —CF$_3$, C$_1$ to C$_6$ alkyl, C$_1$ to C$_6$ alkylaryl, with the proviso that when R$_2$ is —R$_4$ or —OR$_4$, R$_4$ is not hydrogen or C$_1$ to C$_6$ alkyl;

R$_6$, R$_7$, R$_8$, R$_9$, R$_{10}$, R$_{11}$, R$_{12}$, R$_{13}$, R$_{14}$, R$_{15}$, R$_{16}$, R$_{17}$, and R$_{18}$ are each independently H, halogen, —CF$_3$, —(C=O)R$_{20}$, —CN, —OR$_{20}$, —NR$_{20}$R$_{21}$, —NR$_{20}$SO$_2$R$_{22}$, —N=C—N(CH$_3$)$_2$, —N$_{20}$CO$_2$R$_{22}$, —S(O)$_c$R$_{20}$, —SO$_2$NR$_{20}$R$_{21}$, —NO$_2$, aryl, C$_1$ to C$_6$ alkylaryl, —(C=O)OR$_{20}$, —(C=O)NR$_{20}$R$_{21}$, C$_1$ to C$_6$ alkyl, C$_1$ to C$_6$ alkenyl, and C$_1$ to C$_6$ alkynyl;

R$_6$ and R$_7$, and R$_7$ and R$_8$, R$_8$ and R$_9$, R$_9$ and R$_{10}$, R$_{11}$ and R$_{12}$, R$_{12}$ and R$_{13}$, R$_{13}$ and R$_{14}$, R$_{15}$ and R$_{16}$, R$_{16}$ and $R_{17}$, and $R_{17}$ and $R_{18}$ may be taken together to form a five-to-seven-membered alkyl ring, a six-membered aryl ring, a five to seven membered heteroalkyl ring having one heteroatom of N, O, or S, or a five-to six-membered heteroaryl ring have 1 or 2 heteroatoms of N, O, or S;

$R_{19}$ is hydrogen or $C_1$ to $C_3$ alkyl;

$R_{20}$ and $R_{21}$ are each independently hydrogen, $C_1$ to $C_6$ alkyl, aryl, or $C_1$ to $C_6$ alkylaryl, or may be taken together to form a $C_4$ to $C_7$ alkyl ring;

$R_{22}$ is $C_1$ to $C_6$ alkyl, aryl, or $C_1$ to $C_6$ alkylaryl;

A, B, D, E, and F are each independently C or N;

G, I, J, and K are each independently C, N, O, S, or (C=O), with the proviso that there is at most one of O, (C=O), or S per ring;

L and Z are each independently C or N;

M is C, N, or (CO=O);

X is O or S;

a is O or 2;

e is 0, 1 or 2;

d is 0, 1, or 2;

b and c are each independently 0, 1, 2, 3, 4, 5, or 6, with b+c being at most 6;

a broken line indicates the presence optionally of a double bond and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen, hydroxy, cyano, carboxamido, nitro, and $C_1$ to $C_4$ alkoxy, and pharmaceutically acceptable salts thereof.

2. The method of claim 1, wherein $R_1$ is formula II; $R_2$ is —$R_4$, —$OR_4$, $R_4$—$(CH_2)_b$—NH(C=X)—$(CH_2)_c$—, or —$(CH_2)_b$—NH(C=O)—$(CH_2)_c$—$R_4$; $R_3$ is hydrogen or $C_1$ to $C_6$ alkyl; $R_4$ is formula XV or formula XVII; A, B, D. E, and F are each independently C or N; $R_6$, $R_7$, $R_8$, $R_9$, $R_{10}$, $R_{15}$, $R_{16}$, $R_{17}$, $R_{18}$, and $R_{19}$ are each independently hydrogen, halogen, —CN, or —$OR_{20}$; and $R_{20}$ is $C_1$ to $C_6$ alkyl.

3. The method of claim 1 wherein f is 1; g is zero; and $R_3$, $R_6$ $R_7$ are each hydrogen.

4. The method of claim 1, said compound being selected from:

2-[8-(4-Methylpiperazin-1-yl)naphthalen-2-yloxy] nicotinonitrile;

1-(4-Methylpiperazin-1-yl)-7-pyrimidin-5-yl)naphthalene;

7-(5-Cyanopyridin-3-yl)-1-(4-methylpiperazin-1-yl) naphthalene;

1-(Piperazin-1-yl)-7-(pyrimidin-5-yl)naphthalene;

7-(4-Chlorobenzamido)-1-(4-methylpiperazin-1-yl) naphthalene;

7-(3-Methoxyphenyl)1-(4-methylpiperazin-1-yl) naphthalene;

7-(Imidazolo[4,5-b]pyridin-1-yl)-1-(4-methylpiperazin-1-yl)naphthalene;

8-(4-Methylpiperazin-1-yl)naphthalene-2-carboxylic acid 4-chlorobenzylamide;

7-(4-Methoxyphenyl)-1-(4-methylpiperazin-1-yl) naphthalene;

7-(Pyrimidin-2-yloxy)-1-(4-methylpiperazin-1-yl) naphthalene;

8-(1-Methylpiperidin-4-yl)naphthalene-2-carboxylic acid 4-chlorobenzylamide;

1-{7-[5-(2-methoxyphenyl)-[1,2,4]oxadiazol-3-ylmethoxy] -naphthalen-1-yl}-4-methylpiperazine;

1-[7-(5-tert-butyl-[1,2,4]oxadiazol-3-ylmethoxy) naphthalen-1-yl]-4-methylpiperazine;

1-methyl-4-[7-(3-phenyl-[1,2,4]oxadiazol-5-ylmethoxy) naphthalen-1-yl]-piperazine;

1-methyl-4-[7-(5-phenyl-[1,2,4]oxadiazol-3-ylmethoxy) naphthalen-1-yl]-piperazine;

1-{7-[5-(3-methoxyphenyl)-[1,2,4]oxadiazol-3-ylmethoxy] -naphthalen-1-yl}-4-methylpiperazine;

1-{7-[5-(3,5-dimethylisoxazol-4-yl)-[1,2,4]oxadiazol-3-ylmethoxy]-naphthalen-1-yl}-4-methylpiperazine;

1-{7-[3-(4-methoxyphenyl)-[1,2,4]oxadiazol-5-ylmethoxy] -naphthalen-1-yl}-4-methylpiperazine; and 2-[8-(1-methylpiperidin-4-yl)-naphthalen-2-yloxylpyrimidine.

5. A method of inhibiting cell growth in human small cell lung carcinoma comprising administering to a mammal in need of said treatment a cell growth inhibitory effective amount of a compound selected from:

2-[8-(4-Methylpiperazin-1-yl)naphthalen-2-yloxy] nicotinonitrile;

1-(4-Methylpiperazin-1-yl)-7-pyrimidin-5-yl)naphthalene;

7-(5-Cyanopyridin-3-yl)-1-(4-methylpiperazin-1-yl) naphthalene;

1-(Piperazin-1-yl)-7-(pyrimidin-5-yl)naphthalene;

7-(4-Chlorobenzamido)-1-(4-methylpiperazin-1-yl) naphthalene;

7-(3-Methoxyphenyl)1-(4-methylpiperazin-1-yl) naphthalene;

7-(Imidazolo[4,5-b]pyridin-1-yl)-1-(4-methylpiperazin-1-yl)naphthalene;

8-(4-Methylpiperazin-1-yl)naphthalene-2-carboxylic acid 4-chlorobenzylamide;

7-(4-Methoxyphenyl)-1-(4-methylpiperazin-1-yl) naphthalene;

7-(Pyrimidin-2-yloxy)-1-(4-methylpiperazin-1-yl) naphthalene;

8-(1-Methylpiperidin-4-yl)naphthalene-2-carboxylic acid 4-chlorobenzylamide;

1-{7-[5-(2-methoxyphenyl)-[1,2,4]oxadiazol-3-ylmethoxy] -naphthalen-1-yl}-4-methylpiperazine;

1-[7-(5-tert-butyl-[1,2,4]oxadiazol-3-ylmethoxy) naphthalen-1-yl]-4-methylpiperazine;

1-methyl-4-[7-(3-phenyl-[1,2,4]oxadiazol-5-ylmethoxy) naphthalen-1-yl]-piperazine;

1-methyl-4-[7-(5-phenyl-[1,2,4]oxadiazol-3-ylmethoxy) naphthalen-1-yl]-piperazine;

1-{7-[5-(3-methoxyphenyl)-[1,2,4]oxadiazol-3-ylmethoxy] -naphthalen-1-yl}-4-methylpiperazine;

1-{7-[5-(3,5-dimethylisoxazol-4-yl)-[1,2,4]oxadiazol-3-ylmethoxy]-naphthalen-1-yl}-4-methylpiperazine;

1-{7-[3-(4-methoxyphenyl)-[1,2,4]oxadiazol-5-ylmethoxy] -naphthalen-1-yl}-4-methylpiperazine; and 2-[8-(1-methylpiperidin-4-yl)-naphthalen-2-yloxy]-pyrimidine.

* * * * *